(12) United States Patent
Sung et al.

(10) Patent No.: US 9,012,596 B2
(45) Date of Patent: Apr. 21, 2015

(54) COPOLYMERS AND METHODS OF USE THEREOF

(75) Inventors: Hak-Joon Sung, Nashville, TN (US); Lucas L. Hofmeister, Nashville, TN (US); Mukesh Kumer Gupta, Nashville, TN (US); Spencer W. Crowder, Nashville, TN (US); Shann S. Yu, Plano, TX (US); Angela L. Zachman, Lilburn, GA (US); Dae Kwang Jung, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/125,901

(22) PCT Filed: Jun. 16, 2011

(86) PCT No.: PCT/US2011/040708
§ 371 (c)(1),
(2), (4) Date: Dec. 12, 2013

(87) PCT Pub. No.: WO2012/173628
PCT Pub. Date: Dec. 20, 2012

(65) Prior Publication Data
US 2014/0107292 A1    Apr. 17, 2014

(51) Int. Cl.
| | |
|---|---|
| *C08G 63/08* | (2006.01) |
| *A61L 27/22* | (2006.01) |
| *C08G 63/664* | (2006.01) |
| *A61L 27/18* | (2006.01) |
| *C08L 71/02* | (2006.01) |
| *C08G 63/82* | (2006.01) |

(52) U.S. Cl.
CPC ............... *A61L 27/22* (2013.01); *C08G 63/08* (2013.01); *C08G 63/664* (2013.01); *A61L 27/18* (2013.01); *C08L 71/02* (2013.01); *C08G 2261/126* (2013.01)

(58) Field of Classification Search
USPC ................................. 525/54.1, 418; 528/354
See application file for complete search history.

(56) References Cited

U.S. PATENT DOCUMENTS 8,481,651 B2 *   7/2013   Hissink et al. ................ 525/415

FOREIGN PATENT DOCUMENTS

| JP | 2003327814 | 11/2003 |
| KR | 1020100131391 | 12/2010 |
| WO | 2010140869 | 9/2010 |
| WO | WO 2012/173628 | 12/2012 |

OTHER PUBLICATIONS

Peng, Cheng-Liang et al., "Self-assembled star-shaped chlorin-core poly(e-caprolactone)-poly(ethylene glycol) diblock copolymer micelles for dual chemo-photodynamic therapies", Biomaterials vol. 29, No. 26, pp. 3599-3608, Sep. 30, 2008.

Park, Eun Kyoung et al., "Preparation and characterization of methoxy poly(ethylene glycol)/poly(e-caprolactone) amphiphilic block copolymeric nanospheres for tumor-specific folate-mediated targeting of anticancer drugs", Biomaterials, vol. 26, No. 9, pp. 1053-1061, Mar. 31, 2005.

Gimenez, S. et al., "Synthesis, Properties and in Vitro Degradation of Carboxyl-Bearing PCL" Journal of Bioactive and Compatible Polymers, 16: 32, 2001.

Wang, Yu-Cai et al., "Tunable Thermosensitivity of Biodegradable Polymer Micelles of Poly (e-caprolactone) and Polyphosphoester Block Copolymers" Macromolecules, vol. 42, pp. 3026-3032, 2009.

Sosnik, A., "Poly(ethylene glycol)-poly(epsilon-caprolactone) block oligomers as injectable materials" Polymer, vol. 44, pp. 7033-7042, 2003.

PCT International Search Report and Written Opinion for Application No. PCT/US2011/040708 dated Mar. 15, 2012 (9 pages).

Sung, H. J. et al., "The effect of scaffold degradation rate on three-dimensional cell growth and angiogenesis," Biomaterials 25, 5735 (2004).

Tessmar, J. K. et al., "Customized PEG-Derived Copolymers for Tissue-Engineering Applications," Macromolecular Bioscience 7(1), 23-39 (2007).

Goddard, J.M. et al., "Polymer surface modification for the attachment of bioactive compounds," Progress in Polymer Science, 32(7). 698-725 (2007).

Treiser. M. D. et al., "Profiling cell-biomaterials interactions via cell-based fluororeporter imaging." Biotechniques 43, 361 (2007).

Hager, M. et al., "Synthesis of an amphiphilic polymer performed in an oil-in-water microemulsion and in a lamellar liquid crystalline phase," Colloids and Surfaces A: Physicochemical and Engineering Aspects 189 (2001).

Vert, M., "Aliphatic Polyesters: Great Degradable Polymers That Cannot Do Everything." Biomacromolecules, 6(2), 538-546 (2005).

Johnson, P. A. et al., "Interplay of anionic charge, poly(ethylene glycol), and iodinated tyrosine incorporation within tyrosine-derived polycarbonates: Effects on vascular smooth muscle cell adhesion, proliferation, and motility," J Biomed Mater Res A 93, 505 (2009).

Palermo et al., "Transgenic Remodeling of the Contractile Apparatus in the Mammalian Heart," Circ. Res., 1996, 78(3)504-509.

Ponsart et al., "Synthesis Properties and in vitro Degradation of Carboxyl-Bearing PCL," J. Bioact. Compat. Pol., 2001, 16, 32.

Davidson, R., McGraw-Hill, Handbook of Water-Soluble Gums and Resins, 1980.

Ponsart, S. et al., "A Novel Route to Poly(ϵ-caprolactone)-Based Copolymers via Anionic Derivatization." Biomacromolecules, 2000, 1, 275-281.

(Continued)

*Primary Examiner* — Terressa Boykin
(74) *Attorney, Agent, or Firm* — Michael Best & Friedrich LLP

(57) ABSTRACT

Copolymers, such as block copolymers, having at least one block that is a random copolymer of ϵ-caprolactone and α-carboxy-ϵ-caprolactone are described. Also described are methods of using such copolymers, such as, for example, in medical devices.

31 Claims, 21 Drawing Sheets

(56) References Cited

OTHER PUBLICATIONS

Sauer et al., "Reactive Oxygen Species as Signaling Molecules in Cardiovascular Differentiation of Embryonic Stem Cells and Tumor-Induced Angiogenesis," Antiox. Redox Sign., 2005. 7(11-12):1423-1434.

Sawhney, A. S. et al., "Polymer Synthesis," Polymer synthesis, Chapter II.4, In: Partrick Jr. CW Mikos AG, McIntire LV, editors. Frontiers in tissue engineering. Oxford: Pergamon (1998) 83-106.

Sung et al., "Oxidative Stress Produced with Cell Migration Increasses Synthetic Phenotype of Vascular Smooth Muscle Cells," Ann. Biomed. Eng. 2005, 33(11):1546-1554.

Sung et al., "Angiogenic competency of biodegradable hydrogels fabricated from polyethylene glycol-crosslinked tyrosine-derived polycarbonates." Eur. Cells Mater. 15:77-86 (2008).

Sung et al., "Poly(ethylene glycol) as a sensitive regulator of cell survival fate on polymeric biomateriais: the interplay of cell adhesion and pro-oxidant signaling mechanisms," Soft Matter, 2010, 6 (20):5196-5205.

Greene. T. W. et al.. "Protecting Groups in Organic Synthesis", 1999, 3rd edition, John Wiley & Sons.

Wong, W.H. et al., "Synthesis and properties of biodegradable polymers used as synthetic matrices for tissue engineering," Fundamentals of biodegradable polymer scaffolds, 4, In: Atala A, Mooney DJ, Vacanti JP, Langer R, editors. Synthetic biodegradable polymer scaffolds (1997) p. 51-82.

Wang, Y-C. et al., "Turnable Thermosensitivity of Biodegradable Polymer Micelles of Poly (ε-caprolactone) and Polyphosphoester Block Copolymers" Macromolecules, 2009, 42, 3026-3032.

Sung, H. J. et al., "Synthetic Polymeric Substrates as Potent Pro-Oxidant Versus Anti-Oxidant Regulators of Cytoskeletal Remodeling and Cell Apoptosis," J Cell Physiol 218, 549 (2009).

* cited by examiner

A

B

COPOLYMERS AND METHODS OF USE THEREOF

STATEMENT REGARDING FEDERALLY SPONSORED RESEARCH

This invention was made with government support under Grant No. HL091465 awarded by the National Institutes of Health, and Grant No. 1006558 awarded by the National Science Foundation. The United States government has certain rights in the invention.

CROSS-REFERENCE TO RELATED APPLICATIONS

This patent application is a national stage filing under 35 U.S.C. 371 of International Application No. PCT/US2011/040708, filed on June 16, 2011, the disclosure of which is incorporated by reference herein in its entirety. Priority to the application is hereby claimed.

BACKGROUND

The physicochemical and mechanical properties of biomaterials, such as those used in implantable medical devices, can modulate the responses of cells and tissues with which they interact. These biomaterials often include components formed of polymers that can be tailored to have specific physicochemical characteristics that improve the biocompatibility of the material.

SUMMARY

In one aspect, the disclosure provides a compound of formula (I):

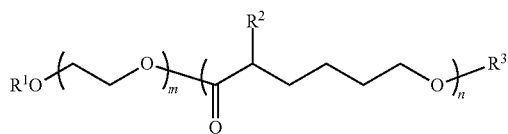

(I)

wherein:
R$^1$ is selected from an alkyl, an acyl and an aryl;
each R$^2$ is independently selected from —H and —COOH;
R$^3$ is selected from —H, an alkyl and an aryl;
m is an integer from about 20 to about 200; and
n is an integer from about 200 to about 2000;
wherein at least one of the R$^2$ substituents is —H and at least one of the R$^2$ substituents is —COOH.

In another aspect, the disclosure provides a block copolymer comprising at least one hydrophilic polymer block, and at least one block comprising a random copolymer of ε-caprolactone and α-carboxy-ε-caprolactone.

In another aspect, the disclosure provides a composition comprising a polymer, as described herein, and at least one compound crosslinked to the polymer.

In another aspect, the disclosure provides a medical device comprising a polymer described herein.

In another aspect, the disclosure provides a method of making a block copolymer comprising providing a hydrophilic polymer comprising a terminal hydroxyl group, reacting said hydrophilic polymer with ε-caprolactone and a catalyst under conditions sufficient to effect ring-opening polymerization of the ε-caprolactone, to form a block copolymer comprising a hydrophilic polymer block and at least one ε-caprolactone block, and carboxylating the α-carbon of at least one ε-caprolactone moiety.

Other aspects and embodiments are encompassed by the disclosure and will become apparent in light of the following description and drawings.

DETAILED DESCRIPTION

Figure 1:
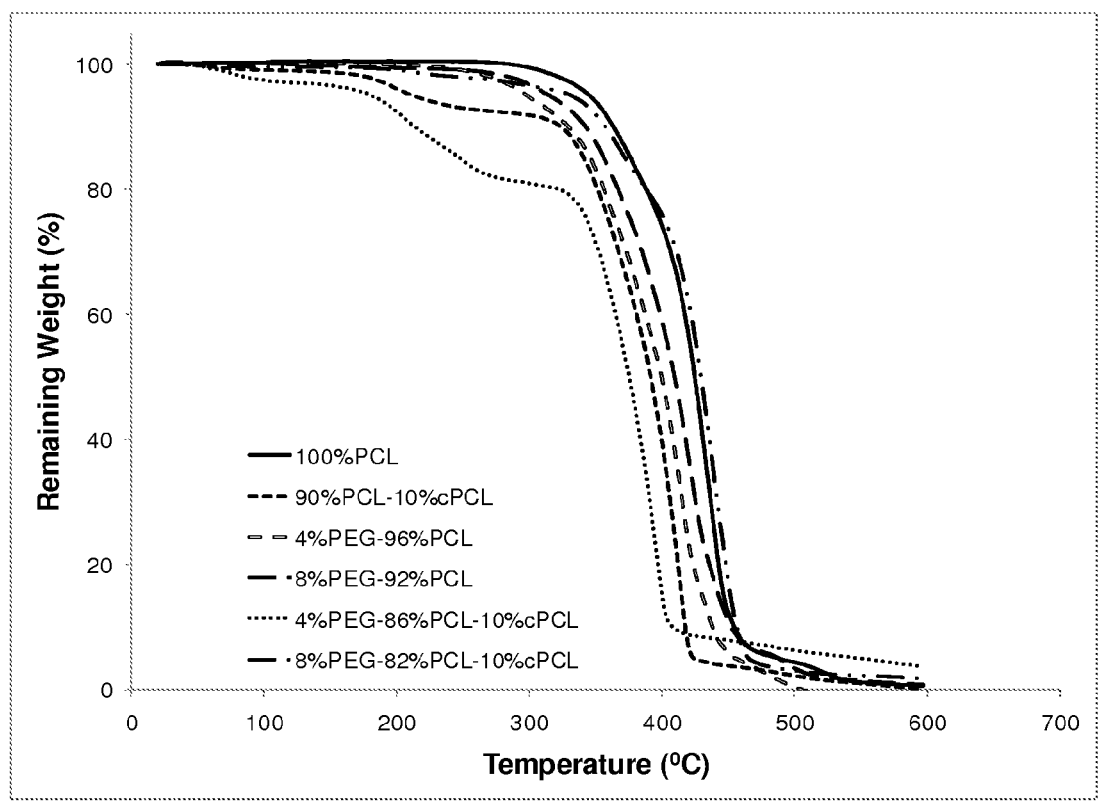
FIG. 1 is a graph showing the results of thermo gravimetric analysis (TGA) of various dry polymer samples.

Described herein are block copolymers comprising at least one block comprising a random copolymer of poly(8-caprolactone) (PCL) and carboxyl-PCL (cPCL). In embodiments, the block copolymers also include at least one hydrophilic block, such as poly(ethylene glycol) (PEG). In one exemplary embodiment, block co-polymers having one PEG block and one block that comprises a random copolymer of PCL and cPCL are disclosed.

Definitions

As used herein, the term "caprolactone" refers to ε-caprolactone, and may be abbreviated CL. The terms caprolactone, ε-caprolactone and CL may be used interchangeably herein.

The term "hydrophilic," as used herein, refers to a moiety (e.g., a polymer) that has a high affinity for water.

A "hydroxy protecting group," as used herein, is well known in the art and includes those described in detail in Protecting Groups in Organic Synthesis, T. W. Greene and P. G. M. Wuts, 3rd edition, John Wiley & Sons, 1999, the entirety of which is incorporated herein by reference. Exemplary hydroxy protecting groups may include, but are not limited to, acetyl (Ac), benzyl (Bn), benzoyl (Bz), ethers (e.g., methoxymethyl ether (MOM) and β-methoxyethoxymethyl ether (MEM)), silyl groups (e.g., trimethylsilyl (TMS), triethylsilyl (TES), triisopropylsilyl (TIPS), tri-iso-propylsilyloxymethyl (TOM) and t-butyldimethylsilyl (TBDMS)), trityl groups (e.g., dimethoxytrityl (DMT) and methoxytrityl (MMT)), and the like.

As used herein, the term "poly(caprolactone-co-α-carboxycaprolactone)", which may be abbreviated as PCL-co-cPCL or PCL/cPCL, refers to a random copolymer of 8-caprolactone and α-carboxy-ε-caprolactone moieties. PCL/cPCL can be one block of a block copolymer, such as a diblock copolymer, a triblock copolymer, and the like.

As used herein, "polydispersity index" (PDI) or "polydispersity" refers to the distribution of molecular mass in a given polymer sample. The PDI is calculated by dividing the weight average molecular weight by the number average molecular weight. It indicates the distribution of individual molecular masses in a batch of polymers. The PDI typically has a value greater than 1, but as the polymer chains approach uniform chain length, the PDI approaches unity (1).

The term "polymer," as used herein, is given its ordinary meaning as used in the art, i.e., a molecular structure featuring one or more repeat units (monomers), connected by covalent bonds. The repeat units may all be identical, or in some cases, there may be more than one type of repeat unit present within the polymer.

The term "providing," as used herein, refers to any means of obtaining a subject item, such as a polymer or one or more blocks of a polymer, from any source including, but not limited to, making the item or receiving the item from another.

"Acyl" refers to a group of the formula —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

"Alkyl" refers to a saturated or unsaturated hydrocarbon chain having 1 to 18 carbon atoms, suitably 1 to 12 carbon atoms, or 1 to 6 carbon atoms, or 1 to 4 carbon atoms. Alkyl groups may be straight or branched. In some embodiments, branched alkyl groups have one or two branches. Unsaturated alkyl groups have one or more double bonds and/or one or more triple bonds. Suitably, unsaturated alkyl groups have one or two double bonds or one triple bond. Alkyl chains may be unsubstituted or substituted with from 1 to about 4 substituents unless otherwise specified.

"Aryl" or "aromatic ring" refers to an aromatic hydrocarbon ring system. Aryl groups are monocyclic or fused bicyclic ring systems. Monocyclic aryl groups contain from about 5 to about 10 carbon atoms, suitably from 5 to 7 carbon atoms, or from 5 to 6 carbon atoms in the ring. Bicyclic aryl groups contain from 8 to 12 carbon atoms, suitably 9 or 10 carbon atoms in the ring. Aryl groups may be unsubstituted or substituted with from 1 to about 4 substituents on the ring.

The above groups, whether alone or part of another substituent, may themselves optionally be substituted with one or more groups selected from themselves and the additional substituents listed below:

Halo: —F, —Cl, —Br, and —I.

Hydroxy: —OH.

Ether: —OR, wherein R is an ether substituent, for example, a $C_{1-7}$ alkyl group (also referred to 15 as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —NO$_2$.

Cyano (nitrile, carbonitrile): —CN.

Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$. as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group. or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. In particular, the cyclic amino groups may be substituted on their ring by any of the substituents defined here, for example carboxy, carboxylate and amido.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and R$^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, NMeCONMe$_2$, —NMeCONEt$_2$, and —NHCONHPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Oxo: =O.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(=O)CH$_3$ and —S(=O)CH$_2$CH$_3$.

Sulfonyl (sulfone): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_a$, —C(=S)N(CH$_3$)$_2$, and —C(=S)NHCH$_2$CH$_3$.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

When peptide sequences are referred to herein, single-letter amino acid codes may be used. For example, and as will be appreciated by the skilled artisan, an oligomer denoted KP$_5$K refers to the peptide Lys-Pro-Pro-Pro-Pro-Pro-Lys.

It is understood that any numerical value recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

Copolymers

Copolymers of the present disclosure include at least one block comprising poly(caprolactone-co-α-carboxycaprolactone) (PCL/cPCL). This block is a random copolymer of caprolactone and α-carboxycaprolactone moieties. In the PCL/cPCL block, at least one monomer unit is caprolactone, and at least one monomer unit is α-carboxycaprolactone. Such blocks may be represented by the following chemical formula:

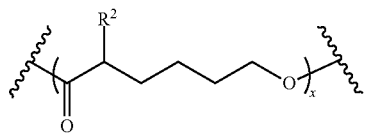

wherein x is an integer representing the number of monomer units in the block, and each R$^2$ is independently selected from —H and —COOH, wherein at least one R$^2$ substituent in the block is —H and at least one is —COOH. The wavy lines at each end of the block represent either a point of attachment to another block of a copolymer, or to a suitable polymer end group.

These polymer blocks may be prepared, for example, via ring-opening polymerization of caprolactone to form a poly(caprolactone) block, followed by carboxylation of the carbon adjacent to the carbonyl group of the caprolactone moiety (the α-carbon). Such carboxylation may be effected, for example, by reaction with a base to deprotonate at the α-carbon, followed by reaction with carbon dioxide. Any base capable of deprotonating the α-carbon may be used; in a suitable embodiment, the base may be lithium diisopropylamide (LDA). The reaction with the base may be carried in a suitable solvent, and the reaction may be carried out at low temperatures. Suitably, the solvent may be an organic solvent such as tetrahydrofuran. In some embodiments, the reaction may be carried out under an inert atmosphere (i.e., substantially free of dioxygen, including but not limited to atmospheres of nitrogen, argon, or other suitably inert gases), and in anhydrous solvents (i.e., substantially free of water). One of skill in the art will appreciate that suitable reaction conditions can be selected based on the particular reaction components employed.

For example, carboxylation of PCL previously was described in Gimenez et al. *J. Bioact. Compat. Pol.* 2001, 16, 32-46, the complete disclosure of which is herein incorporated by reference for all purposes. PCL polymers were dissolved in anhydrous tetrahydrofuran at low temperature (−78° C.) and treated with LDA under an inert atmosphere. Carboxylation of the resulting product was effected by addition of CO$_2$, followed by quenching to yield the random copolymers of PCL and cPCL.

As one of skill in the art will recognize, changing the amount of base (e.g., LDA) that is added to the starting polymers may produce products with varying —COOH contents. Specifically, increasing the amount of base will produce polymers with more —COOH moieties, and thus an increased degree of functionalization, while smaller amounts of base will produce polymers with fewer —COOH moieties. In the copolymers described herein, the PCL/cPCL blocks may include about 70-99% caprolactone moieties and about 1-30% α-carboxycaprolactone moieties. For example, the PCL/cPCL block may include about 75-95% caprolactone moieties and about 5-25% α-carboxycaprolactone moieties. In some embodiments, the PCL/cPCL blocks may include at least about 70%, at least about 75%, at least about 80%, at least about 85%, at least about 90%, at least about 95%, or at least about 99% caprolactone moieties. In some embodiments, the PCL/cPCL blocks may include up to about 1%, up to about 5%, up to about 10%, up to about 15%, up to about 20%, up to about 25% or up to about 30% α-carboxycaprolactone moieties. In some embodiments, the PCL/cPCL blocks may include at least one caprolactone moiety and at least one α-carboxycaprolactone moiety.

The PCL blocks to be used in the carboxylation reaction described above may be derived from any suitable source. In some embodiments, PCL polymers may be commercially available. In some embodiments, PCL polymers may be synthesized, e.g., via ring-opening polymerization. Such reactions previously have been described (see, e.g., Wang et al. *Macromolecules* 2009, 42, 3026-3032, the complete disclosure of which is herein incorporated by reference for all purposes). The ring-opening polymerization may be catalyzed by any suitable catalyst known in the art or hereinafter devised, including, but not limited to, metal-containing compounds, such as metal-alkoxides, metal-carboxylates, and the like. For example, commonly used catalysts may include, but are not limited to, tin or aluminum complexes, such as tin or aluminum alkoxides, and tin(II) ethylhexanoate (also known as tin(II) octoate).

The PCL/cPCL polymer blocks may be of any suitable molecular weight. In embodiments, the PCL/cPCL block may have a molecular weight of from about 5 kDa to about 250 kDa. For example, the PCL/cPCL block may have a molecular weight of from about 20 kDa to about 200 kDa, from about 25 kDa to about 150 kDa, from about 30 kDa to about 125 kDa, from about 40 kDa to about 105 kDa, from about 50 kDa to about 90 kDa, or from about 70 kDa to about 80 kDa. In embodiments, the PCL/cPCL block may have a molecular weight of at least about 5 kDa, at least about 10 kDa, at least about 15 kDa, at least about 20 kDa, at least about 25 kDa, at least about 30 kDa, at least about 35 kDa, at least about 40 kDa, at least about 45 kDa, at least about 50 kDa, at least about 55 kDa, at least about 60 kDa, at least about 65 kDa, at least about 70 kDa, at least about 75 kDa, at least about 80 kDa, at least about 85 kDa, at least about 90 kDa, at least about 95 kDa, at least about 100 kDa, at least about 110 kDa, at least about 120 kDa, at least about 130 kDa, at least about 140 kDa, at least about 150 kDa, or at least about 175 kDa. In embodiments, the PCL/cPCL block may have a molecular weight of less than about 200 kDa, less than about 175 kDa, less than about 150 kDa, less than about 140 kDa, less than about 130 kDa, less than about 120 kDa, less than about 110 kDa, less than about 100 kDa, less than about 90 kDa, less than about 80 kDa, less than about 70 kDa, less than about 60 kDa, less than about 50 kDa, less than about 45 kDa, less than about 40 kDa, less than about 35 kDa, less than about 30 kDa, less than about 25 kDa, less than about 20 kDa, or less than about 15 kDa, less than about 10 kDa.

Ring-opening polymerization reactions generally may be conducted in the presence of an initiator, such as an alcohol. When generating PCL homopolymers, a suitable initiator may comprise an alcohol, including, but not limited to, benzyl alcohol. For preparation of block copolymers, an initiator may comprise another polymer block, including, but not limited to, a polymer block having a terminal hydroxyl group. Exemplary polymers may include poly(ethylene glycol) polymers, which may or may not include a substituent on one of the two terminal hydroxyl moieties. For example, one of the two terminal hydroxyl groups may be protected with an alkyl, acyl or aryl group. Any suitable hydroxy protecting group may be used. Suitably, mono-methoxy poly(ethylene glycol) may be used to initiate caprolactone polymerization to generate a PEG-PCL block copolymer. This product may be carboxylated to yield a PEG-b-PCL/cPCL block copolymer.

The copolymers described herein include block copolymers, which include diblock copolymers, triblock copolymers and the like. Each of the blocks of the copolymer may themselves be copolymers of one or more monomer units, e.g., random copolymers of one or more monomers. In suitable embodiments, the copolymers may be diblock copolymers, including one block of a hydrophilic polymer and one block comprising a random copolymer of PCL and cPCL. The polymers may also be triblock copolymers, in which one of the blocks is a PCL/cPCL random copolymer. The two other blocks of the triblock copolymer may be the same or different.

Block copolymers can be prepared by any technique currently known or hereinafter devised. For example, one method of preparing a block copolymer may include providing separate polymer blocks and linking them together via a covalent bond. Another suitable method may include providing one polymer block and synthesizing the second polymer block using the first block as an initiator. Such an embodiment was described above regarding PEG-b-PCL/cPCL.

In block copolymers in which one block is PCL/cPCL, the other block may be a hydrophilic polymer block. The hydrophilic polymer block may be a homopolymer or may itself be a copolymer of several different monomers. Suitable hydrophilic polymers may include, but are not limited to, poly (ethylene glycol), poly(propylene oxide), partially or fully hydrolyzed poly(vinyl alcohol), poly(vinylpyrrolidone), poly (ethyloxazoline), poly(ethylene oxide)-co-poly(propylene oxide) block copolymers (poloxamers and meroxapols), poloxamines, polyethyleneimines, polyionenes, polyiminocarboxylates, gelatin, unsaturated ethylenic mono or dicarboxylic acids, carboxymethyl cellulose, hydroxyalkylated celluloses such as hydroxyethyl cellulose and methylhydroxypropyl cellulose, polypeptides such as polylysines, polyarginines and polyglutamic acids, polysaccharides or carbohydrates such as hyaluronic acid, dextran, heparan sulfate, chondroitin sulfate, heparin, and alginate, and proteins such as gelatin, collagen, albumin, or ovalbumin, or copolymers or blends thereof. As used herein, "celluloses" may include, but are not limited to, cellulose and derivatives of the types described above; "dextran" may include, but is not limited to, dextran and similar derivatives thereof. A listing of hydrophilic polymers can be found in Handbook of Water-Soluble Gums and Resins, R. Davidson, McGraw-Hill (1980), the complete disclosure of which is herein incorporated by reference for all purposes. Such polymers may be commercially available, may be isolated from natural sources, or may be synthesized using standard polymerization procedures, including, but not limited to, anionic polymerization, cationic polymerization, ring-opening polymerization, ring-opening metathesis polymerization, radical polymerization, controlled radical polymerization (e.g., nitroxide-mediated radical polymerization, atom transfer radical polymerization (ATRP), reversible addition-fragmentation chain transfer polymerization (RAFT), catalytic chain transfer polymerization and the like), and any other suitable method. In suitable embodiments, the hydrophilic polymer block is a PEG polymer block.

The hydrophilic polymer block may be of a range of molecular weights. For example, block may have a molecular weight of from about 0.5 kDa to about 50 kDa, from about 1 kDa to about 45 kDa, from about 2 kDa to about 40 kDa, from about 3 kDa to about 30 kDa, from about 4 kDa to about 20 kDa, or from about 5 kDa to about 10 kDa. In embodiments, the block may have a molecular weight of at least about 1 kDa, at least about 2 kDa, at least about 3 kDa, at least about 4 kDa, at least about 5 kDa, at least about 6 kDa, at least about 7 kDa, at least about 8 kDa, at least about 9 kDa, at least about 10 kDa, at least about 15 kDa, at least about 20 kDa, at least about 25 kDa, at least about 30 kDa, at least about 35 kDa, at least about 40 kDa, or at least about 45 kDa. In embodiments, the hydrophilic block may have a molecular weight of less than about 50 kDa, less than about 45 kDa, less than about 40 kDa, less than about 35 kDa, less than about 30 kDa, less than about 25 kDa, less than about 20 kDa, less than about 15 kDa, less than about 10 kDa, less than about 9 kDa, less than about 8 kDa, less than about 7 kDa, less than about 6 kDa, less than about 5 kDa, less than about 4 kDa, less than about 3 kDa, or less than about 2 kDa. In embodiments, the hydrophilic polymer block is a PEG polymer block, which may be of a molecular weight from about 1 kDa to about 10 kDa, from about 2 kDa to about 7.5 kDa, from about 3 kDa to about 6 kDa, about 1 kDa, about 2 kDa, about 3 kDa, about 4 kDa, about 5 kDa, about 6 kDa, about 7 kDa, about 8 kDa, about 9 kDa or about 10 kDa.

Exemplary polymers include those of formula (I):

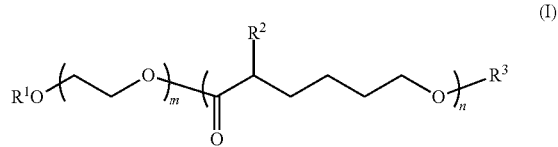

wherein:

$R^1$ is selected from alkyl, acyl and aryl;

each $R^2$ is independently selected from —H and —COOH;

$R^3$ is selected from hydrogen, alkyl and aryl;

m is an integer from about 20 to about 200; and n is an integer from about 200 to about 2000;

wherein at least one of the $R^2$ substituents is —H and at least one is —COOH.

One of skill in the art will appreciate that the integers m and n may be selected to correspond to the molecular weight values described above for the PEG block and the PCL/CPCL block. In embodiments, m may be an integer from about 20 to about 200, from about 50 to about 175, from about 70 to about 140, about 20, about 30, about 40, about 50, about 60, about 70, about 80, about 90, about 100, about 110, about 115, about 120, about 130, about 140, about 150, about 160, about 170, about 180, about 190 or about 200. In embodiments, n may be an integer from about 200 to about 2000, from about 250 to about 1300, from about 250 to about 1100, from about 350 to about 900, from about 450 to about 800, from about 800 to about 1000, from about 600 to about 700, about 200, about 300, about 400, about 500, about 600, about 700, about 800, about 900, about 1000, about 1100, about 1200, about 1300, about 1400, about 1500, about 1600, about 1700, about 1800, about 1900 or about 2000.

An exemplary synthesis of a block copolymer is illustrated below in Scheme 1.

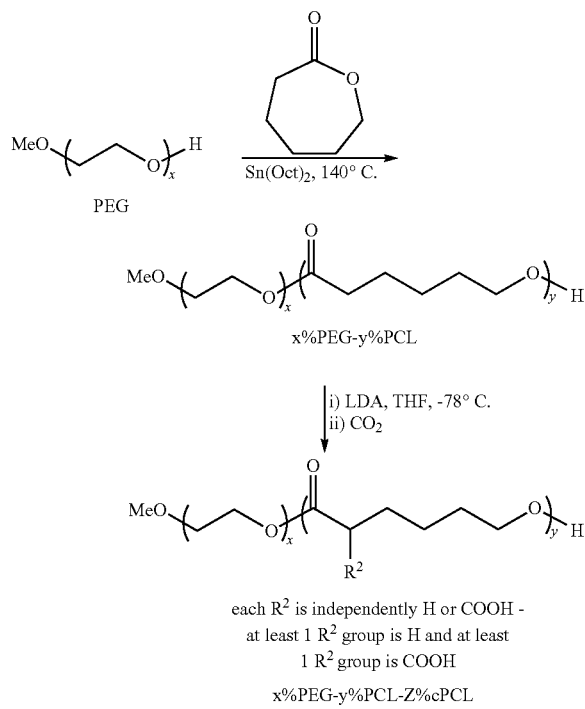

Scheme 1. Synthesis of an exemplary copolymer.

In the above scheme and elsewhere herein, copolymers of x mol % PEG, y mol % PCL and z mol % cPCL are denoted x % PEG-y % PCL-z % cPCL or x % PEG-b-y % PCL-z % cPCL. In such abbreviations, it is understood that the polymer is a block copolymer wherein one block is PEG and the other block is a random copolymer of PCL and cPCL. Copolymers that may be suitable for the compositions and methods described herein include, but are not limited to, 4% PEG-86% PCL-10% cPCL and 8% PEG-82% PCL-10% cPCL. These copolymers may be particularly useful for cardiovascular applications, as described herein.

Without being limited as to theory, it is believed that some of the copolymers described herein have physical and mechanical properties that make them useful as biomaterials, such as materials used to make implantable medical devices. PCL is a semi-crystalline, hydrophobic polymer that exhibits slow degradation kinetics with biocompatible byproducts; PEG is a hydrophilic polymer that may absorb water and repel nonspecific protein adsorption through steric exclusion; and cPCL may further promote water absorption and facilitate cell attachment by providing a negative charge at the surface. Accordingly, the presence of cPCL may buffer the repellent character of PEG while simultaneously increasing hydrophilicity of the resulting material.

Polymers described herein may include a variety of end groups. For example, a polymer may have end groups selected from hydroxy, alkoxy, aryloxy and ester groups. The end group of the polymer may not be further modified after polymer synthesis, or may be modified, e.g., to include a capping group or a protecting group. For example, a hydroxy end group can be alkylated or arylated to form an alkoxy- or aryloxy-capped polymer.

Once prepared, the polymers described herein may be analyzed by methods known in the art, including, but not limited to, nuclear magnetic resonance (NMR), gel permeation chromatography (GPC), differential scanning calorimetry (DSC), thermogravimetric analysis (TGA), dynamic mechanical analysis (DMA), measurements of the water contact angle, rheometry, photoelectron spectroscopy, infrared (IR) spectroscopy, matrix-assisted laser desorption/ionization time-of-flight mass spectrometry (MALDI-TOF-MS), and the like.

The various polymers described herein also may be incorporated into, or derivatized to form other compositions. For example, polymers comprising at least one block of PCL/cPCL may include free —COOH moieties on the cPCL groups, which may react with one or more other compounds to form a covalent bond between the polymer and the one or more other compounds. Such other molecules include, but are not limited to, polymers (e.g., hydrophilic polymers), peptides, pharmaceutical compounds, diagnostic compounds, and the like, or combinations thereof. Such compounds may be directly covalently linked to the polymers, or may be attached to the polymers via a linker.

Alternatively or additionally, other compounds can be used as crosslinkers that may link two or more polymers to form a polymer network. In such cases, the crosslinker may include any suitable compound having at least two reactive moieties that can each react with a —COOH group, which may include, for example, amines, hydrazides, hydroxides, thiols, diols, or any other suitable functional group that reacts with a —COOH group. Exemplary crosslinkers may include, but are not limited to, hydrophilic polymers (e.g., hydrophilic polymers with at least two functional groups, such as PEG dihydrazide, PEG diamine, PEG-diester-dithiol, poly(vinyl alcohol), and the like), diols and polyols (e.g., glycerol, glucose, sorbitol, pentaerythritol, ethylene glycol, diethylene glycol and the like), diamines (e.g., ethylene diamine, lysine, and the like), amino hydroxy compounds (e.g., 2-amino-2-methyl-1-propanol, aminoethanol and the like), bis-thiols, and others. The crosslinkers may themselves include additional compounds as pendant functional groups, or may include, for example, peptide sequences.

In embodiments in which polymers described herein, such as block copolymers PEG-PCL/cPCL, are crosslinked with a hydrophilic polymer having at least two reactive moieties (such as PEG-dihydrazide), the resulting products may be hydrogels. The properties of such hydrogels may be different from the unreacted PEG-PCL/cPCL polymers. For example, crosslinking with PEG-dihydrazide may increase the hydrophilicity of the polymer network, and may improve irrigation of the scaffold.

Compounds may be used to crosslink the polymers according to methods currently known or hereinafter devised. For example, crosslinking reactions may require the use of one or more suitable crosslinking agents, including, but not limited to, carbodiimides, and the like.

Methods of Use

Polymers described herein may be useful, for example, in medical devices. In some embodiments, suitable medical devices may be implantable medical devices. Medical devices that may be manufactured from polymers described herein, or coated with polymers described herein, may include, but are not limited to, cardiovascular stents, stent grafts, urethral stents, bile duct stents, catheters, cardiac patches, guide wires, pacemaker leads, bone screws, sutures and prosthetic heart valves, and the like. Polymers may also be useful in generating artificial skin or artificial bone.

Cardiovascular disease, specifically atherosclerosis, remains a leading cause of death in developed countries. Atherosclerosis is a multifactorial disease that results in a narrowing, or stenosis, of a vessel lumen. Briefly, pathologic inflammatory responses resulting from vascular endothelium injury causes monocytes and vascular smooth muscle cells (VSMCs) to migrate from the sub endothelium and into the arterial wall's intimal layer. There the VSMC proliferate and lay down an extracellular matrix causing vascular wall thickening and reduced vessel patency.

Cardiovascular disease caused by stenotic coronary arteries is commonly treated using either coronary artery by-pass graft (CABG) surgery or angioplasty. Angioplasty is a percutaneous procedure wherein a balloon catheter is inserted into the coronary artery and advanced until the vascular stenosis is reached. The balloon is then inflated restoring arterial patency. One angioplasty variation includes arterial stent deployment. Briefly, after arterial patency has been restored, the balloon is deflated and a vascular stent is inserted into the vessel lumen at the stenosis site. The catheter is then removed from the coronary artery and the deployed stent remains implanted to prevent the newly opened artery from constricting spontaneously. However, balloon catheterization and stent deployment can result in vascular injury ultimately leading to VSMC proliferation and neointimal formation within the previously opened artery. This biological process whereby a previously opened artery becomes re-occluded is referred to as restenosis.

The introduction of intracoronary stents into clinical practice has dramatically changed treatment of obstructive coronary artery disease. Since having been shown to significantly reduce restenosis as compared to percutaneous transluminal coronary angioplasty (PTCA) in selected lesions, the indication for stent implantation was been widened substantially. As a result of a dramatic increase in implantation numbers worldwide in less selected and more complex lesions, in-stent restenosis (ISR) has been identified as a new medical problem with significant clinical and socioeconomic implications. The number of ISR cases is growing: from 100,000 patients treated worldwide in 1997 to an estimated 150,000 cases in 2001 in the United States alone. ISR is due to a vascular response to injury, and this response begins with endothelial denudation and culminates in vascular remodeling after a significant phase of smooth muscle cell proliferation.

Additionally, recent advances in in situ drug delivery have led to the development of implantable medical devices specifically designed to provide therapeutic compositions to remote anatomical locations. Perhaps one of the most exciting areas of in situ drug delivery is in the field of intervention cardiology. Vascular occlusions leading to ischemic heart disease are frequently treated using percutaneous transluminal coronary angioplasty (PTCA) whereby a dilation catheter is inserted through a femoral artery incision and directed to the site of the vascular occlusion. The catheter is dilated and the expanding catheter tip (the balloon) opens the occluded artery restoring vascular patency. Generally, a vascular stent is deployed at the treatment site to minimize vascular recoil and restenosis. However, in some cases stent deployment leads to damage to the intimal lining of the artery which may result in vascular smooth muscle cell hyperproliferation and restenosis. When restenosis occurs it is necessary to either re-dilate the artery at the treatment site, or, if that is not possible, a surgical coronary artery bypass procedure must be performed.

Generally, implantable medical devices are intended to serve long term therapeutic applications and are not removed once implanted. In some cases it may be desirable to use implantable medical devices for short term therapies. However, their removal may require highly invasive surgical procedures that place the patient at risk for life threatening complications. Therefore, it may be desirable to have medical devices designed for short term applications that degrade via normal metabolic pathways and are reabsorbed into the surrounding tissues.

Implanted medical devices that are coated with biodegradable biocompatible polymers offer substantial benefits to the patient. Reduced inflammation and immunological responses promote faster post-implantation healing times in contrast to uncoated medical devices. Polymer-coated vascular stents, for example, may encourage endothelial cell proliferation and therefore integration of the stent into the vessel wall. Loading the coating polymers with appropriate drugs may also advantageous in preventing undesired biological responses.

Polymers described herein can be evaluated for their potential use in medical devices, such as implantable medical devices, using a number of methods. For example, growth of various cell lines on polymer scaffolds can be evaluated in order to gain insights in to biocompatibility. Such assays may monitor, for example, cell growth and proliferation, cell morphology, production of reactive oxygen species and protein expression levels. These assays may be carried out with any known cell lines. For example, for evaluating the potential of polymers for use in cardiovascular stents, patches, or other devices for use in cardiovascular applications, the growth of cardiac cell lines such as human coronary artery vascular smooth muscle cells (HCASMCs) and human coronary artery endothelial cells (HCAECs) can be evaluated. In general, healthy vascular smooth muscle cells (SMCs) proliferate at a very low rate and assume a contractile phenotype that is characterized by strong smooth muscle myosin heavy chain (smMHC) expression, and a spindle-like morphology. In contrast, unhealthy, "dedifferentiated" SMCs assume a circular cobble stone-like, synthetic phenotype in which smMHC expression is significantly down-regulated. To test the ability of the different polymers to discourage a pathogenic, synthetic phenotype, smMHC expression and cell morphology can be evaluated.

Copolymers that may be suitable for the methods described herein, such as cardiovascular applications, include but are not limited to 4% PEG-86% PCL-10% cPCL and 8% PEG-82% PCL-10% cPCL.

Polymers may also be evaluated for their ability to promote differentiation of stem cells. For example, for evaluation of potential for use in cardiovascular applications, the differentiation of embryonic stem cells into, for example, cardiomyocytes can be tested. For example, polymers may be electrospun to generate polymer scaffolds, on which stem cells, such as embryonic stem cells (ESCs), can be cultured. The ability of the ESCs to differentiate into healthy cardiomyocytes can then be evaluated.

The following non-limiting Examples are intended to be purely illustrative, and show specific experiments that were carried out in accordance with the disclosure.

EXAMPLES

Materials and Methods

ε-caprolactone and benzyl alcohol were purchased from Alfa Aesar (Ward Hill, Mass., USA). Tin (II) ethyl hexanoate $(Sn(Oct)_2)$, benzyl alcohol, monomethoxypoly(ethylene glycol) (PEG) ($M_n$=5000), anhydrous tetrahydrofuran (THF), lithium diisopropylamide (LDA) (2M in THF/n-heptane), anhydrous toluene, dichloromethane and diethyl ether were purchased from Sigma-Aldrich Chemicals (St. Louis, Mo., USA), and were used as purchased unless otherwise noted. ε-caprolactone was dried and distilled over $CaH_2$ immediately before polymerization. Tin (II) ethyl hexanoate was distilled under high vacuum. Benzyl alcohol was dried and distilled over $CaH_2$.

Copolymers of x mol % PEG, y mol % PCL, and z mol % cPCL are identified in the following examples as x % PEG-y % PCL-z % cPCL, where it is expressly understood that PEG-PCL is a block copolymer and cPCL addition is random within the PCL subunit.

Polymer samples were prepared as described below in Examples 2-6. Characterization of the resulting polymers by GPC revealed that the $M_n$ ranged from 65-113 kDa, relative to monodisperse PMMA standards (Table 4).

For polymer characterization, gel permeation chromatography (GPC) was performed on a Tosoh Biosciences TSKGel SuperHZ-M mixed bed column (4×106 Da exclusion limit, THF mobile phase) incubated at 40° C., with a Shimadzu SPD-10A UV detector and RID-10A refractive index detector (Shimadzu Scientific Instruments, Columbia, Md.), and a Wyatt miniDAWN Treos multi-angle light scattering detector (MALS, Wyatt Technology, Santa Barbara, Calif.). Molecular weights ($M_n$) and polydispersities ($M_w/M_n$) were determined against monodisperse poly(methyl methacrylate) standards (PMMA, Varian Inc., Palo Alto, Calif.). $^1$H NMR spectra were recorded on a Bruker 400 MHz spectrometer with $CDCl_3$ as solvent.

For testing mechanical and thermal properties, solvent cast films were prepared at 5% weight/volume (w/v) in dichloromethane in a 100 mm glass Petri dish, left at room temperature in air overnight, and then placed under vacuum to remove excess solvent. For biological experiments, cover glass samples were prepared by spin coating (WS-650SZ-6NPP/Lite Spin Coater, Laurell Technologies, North Wales, Pa.) at 1% w/v in 70/30 chloroform/dimethylformamide onto 15 mm glass cover slips at 4,000 RPM for 30 seconds. Samples were placed under vacuum for at least two days before use. Samples for cellular interaction experiments were sterilized under UV light for 1 hour.

For cell growth experiments, polymer samples were prepared by electrospinning a polymer solution in a solvent mixture (e.g., a mixture of chloroform and methanol). A solution was continuously supplied using a syringe pump at a given voltage to produce electrospun fibers, which were collected over glass cover slips placed on a rotating mandrel. The scaffolds were dried under vacuum and sterilized by UV irradiation before cell culture. For further details, see, e.g., Example 13.

Human coronary artery vascular smooth muscle cells (HCASMCs, passages 6-8) were cultured in Dulbecco's Modified Eagle's Medium (DMEM, Gibco Cell Culture, Carlsbad, Calif.) supplemented with 10% heat-inactivated fetal bovine serum (FBS, Gibco), 1% penicillin-streptomycin (Gibco), and 1% L-glutamine (Gibco). Human coronary artery endothelial cells (HCAECs, passage 7) were cultured in MesoEndo Growth Medium (Cell Applications, Inc., San Diego, Calif.) supplemented with 10% FBS and 1% penicillin-streptomycin. Cells were purchased from Cell Applications, Inc. (San Diego, Calif.). Cells were cultured for three days on test polymer samples before end point experiments.

For immunofluorescence staining, cells were fixed in 4% paraformaldehyde (Sigma) in $dH_2O$ and incubated with primary antibody (1:100) overnight at 4° C. To measure proliferation, cells were incubated with 5-bromo-2'-deoxyuridine (BrdU, Sigma) at 20 μM for 16 hours. Incorporated BrdU in proliferating cells was detected by staining with primary rat anti-human BrdU antibodies (1:100, Abcam, Cambridge, Mass.), followed by addition of secondary DyLight594-conjugated goat anti-rat (1:50, Jackson Immunoresearch, West Grove, Pa.) antibodies. To evaluate a healthy contractile phenotype in HCASMCs, expression of smooth muscle myosin heavy chain (smMHC) was detected by staining with primary mouse anti-human smMHC antibodies (1:100, Abcam), followed by addition of secondary TRITC-conjugated goat anti-mouse (1:50, Abcam) antibodies. To evaluate inflammatory action of HCAECs, expression of vascular cell adhesion molecule (VCAM)-1 was detected by staining with APC-conjugated anti-human VCAM-1 antibodies (5 μg/mL, CD 106, BioLegend, San Diego, Calif.). Cell nuclei were counterstained with Hoechst 33258 (5 μg/mL, Sigma) in all of the aforementioned types of fluorescence staining. Cells were imaged under a Nikon Eclipse Ti inverted fluorescence microscope (Nikon Instruments Inc, Melville, N.Y.). Relative protein expression was quantified by measuring fluorescence intensity from antibody staining, which was normalized to cell number from Hoechst nucleus staining using ImageJ. Cell proliferation was calculated by determining the percent of BrdU-positive cells in the total number of cells (%) (n=12).

For embryonic stem cell assays, mouse germ line competent CGR8 embryonic stem cells (European Collection of Cell Cultures, Salisbury, United Kingdom) were used. To monitor cardiomyogenic differentiation, CGR8 cells were stably transfected with a construct in which the red fluorescent protein gene was fused to a nuclear localization signal (DsRed-Nuc) under the control of the α-myosin heavy chain (α-MHC) promoter. Therefore, α-MHC expressing cells are marked with red nuclear fluorescence, allowing a visual, quantitative assessment of differentiating cardiomyocytes (see, e.g., Palermo et al. *Circ. Res.* 1996; 78(3):504-509.). Cells were cultured in DMEM supplemented with 10% refined fetal calf serum (Invitrogen), 0.1 mM nonessential amino acids (Sigma, St. Louis, Mo., USA), 0.05 mM β-mercaptoethanol, and 100 U/mL leukemia inhibitory factor (LIF) (Chemicon International Inc., Temecula, Calif.), and maintained in 37° C. under 5% $CO_2$ before use.

To measure α-MHC expression, total RNA was extracted from ESCs using the RNeasy Mini Kit (Qiagen, Valencia, Calif.) according to the manufacturer's instructions and subsequently treated with RNase-free DNase I (Qiagen). Equal concentrations of RNA were then reverse-transcribed using the SuperScript III First-Strand Synthesis SuperMix (Invitrogen). Real time-PCR was performed on the Bio-Rad ICyclerIQ (Hercules, Calif.) using the iQ SYBR Green Supermix (Bio-Rad) (n=3) and the following primers (all purchased from Sigma-Aldrich): GAPDH forward 5'-CTCACTCAA-GATTGTCAGCAATG-3' and GAPDH reverse 5'-GAGG-GAGATGCTCAGTGTTGG-3; α-MHC forward 5'-TACACTCTTCTCTACCTATGCTTCT-3' and α-MHC reverse 5'-CACTATCTTCTTGAACTCAATGC-3'. Each primer pair was tested and its melt curve was analyzed to ensure that only a single amplicon was generated. Each test sample was assayed for target gene or glyceraldehyde 3-phosphate dehydrogenase (GAPDH, reference gene) and the average value was used as the cycle threshold (CT) (i.e., the number of cycles needed for the fluorescent signal to exceed the background level). To perform statistical analyses and for graphical representation, target gene CT values (A) and GAPDH CT values (B) were both expressed as exponents of 2, and data represented as the ratio of 2A/2B, or 2(A-B). To measure α-MHC protein expression, the red fluorescence intensity of ESCs transfected with the α-MHC-DsRed fusion was measured using a fluorescence plate reader (Tecan infinite F500) (n=4). The fluorescence intensity was normalized to the corresponding cell number measured from Hoechst nucleus staining.

In all experiments, results are presented as means±standard error of the mean (SEM). Results from each experiment were analyzed using single factor analysis of variance and comparisons between individual sample groups were performed using an unpaired Student's t-test. For all statistics, $p<0.05$ was considered statistically significant.

Example 1

Synthesis of PCL

PCL was synthesized via ring-opening polymerization of ε-caprolactone (CL) in bulk using benzyl alcohol as the initiator and $Sn(Oct)_2$ as the catalyst, similar to methods described in previous literature with slight modification (Y—C Wang, Y. Li, X-Z. Yang, Y-Y. Yuan, Li-F. Yan, and J. Wang, "Tunable Thermosensitivity of Biodegradable Polymer Micelles of Poly(ε-caprolactone) and Polyphosphoester Block Copolymers" Macromolecules 2009, 42, 3026-3032). Briefly, CL ($100 \times 10^{-3}$ mol, 11.4 g, 10.96 mL), $Sn(Oct)_2$ ($100 \times 10^{-6}$ mol, 40 mg), benzyl alcohol ($100 \times 10^{-6}$ mol, 0.10 g, 0.10 ml) were placed in a previously flame dried, 100 mL round bottom flask, and polymerization temperature was increased up to 140° C. After 4 hour reaction, polymerization was stopped and the resulting polymer was dissolved in dichloromethane and precipitated into excess of diethyl ether. $^1$H NMR ($CDCl_3$)=δ 4.06 (t, 3H, —$OCH_2$), 2.31 (t, 2H, —$CH_2$), 1.66 (m, 2H, —$CH_2$), 1.37 (m, 4H, —$CH_2$) ppm.

Example 2

Synthesis of 4% PEG-96% PCL

A 4% PEG-96% PCL diblock copolymer was synthesized by ring opening polymerization similar to methods described in previous literature with slight modification (Sosnik et al. Polymer, 2003, 44, 7033-7042). PEG ($0.05 \times 10^{-3}$ mol, 0.25 g, $M_n$=5,000 g/mol), CL ($84.21 \times 10^{-3}$ mol, 9.6 g, 9.3 mL) and $Sn(Oct)_2$ ($84.21 \times 10^{-6}$ mol, 34 mg) were placed in a previously flame dried, 100 mL round bottom flask, and polymerization temperature was increased up to 140° C. After 4 h of reaction time, polymerization was stopped and the resulting polymer was dissolved in dichloromethane and precipitated in an excess of diethyl ether. $^1$H NMR ($CDCl_3$)=δ 4.06 (t, 3H, —$OCH_2$), 3.65 (s, 4H, —$OCH_2$), 2.31 (t, 2H, —$CH_2$), 1.66 (m, 2H, —$CH_2$), 1.37 (m, 4H, —$CH_2$) ppm.

Example 3

Synthesis of 8% PEG-92% PCL

A copolymer, 8% PEG-92% PCL was synthesized following a similar process as that used to synthesize 4% PEG-96% PCL described in Example 2, adjusting only for the different ratio of PEG to PCL. $^1$H NMR ($CDCl_3$)=δ 4.06 (t, 3H, —$OCH_2$), 3.65 (s, 4H, —$OCH_2$), 2.31 (t, 2H, —$CH_2$), 1.66 (m, 2H, —$CH_2$), 1.37 (m, 4H, —$OCH_2$) ppm.

Example 4

Synthesis of 90% PCL-10% cPCL copolymer

A 90% PCL-10% cPCL copolymer was synthesized according to the previously reported methods (Ponsart et al. J. Bioact. Compat. Pol. 2001, 16, 32). PCL (8.0 g, 0.067 mol) in 400 mL of anhydrous THF was added to a previously flame-dried round bottom flask under dry nitrogen. The stirred solution was placed in dry ice/acetone bath and degassed with three pump-thaw cycles. A solution of LDA, 2 M in THF/n-heptane (33.5 mL, 0.067 mol: 1 equivalent per monomeric unit), was added dropwise with a syringe into the degassed solution and the reaction mixture was stirred for 30 minutes. The addition of concentrated $H_2SO_4$ to dry $Na_2CO_3$ generated a stream of dry $CO_2$ gas and was allowed to bubble through the solution for 30 min. An aqueous solution of $NH_4Cl$ was added to the flask to quench the reaction mixture. The resulting solution was acidified using an aqueous solution of concentrated HCl down to pH 2-3. The resulting copolymer was extracted twice with $2 \times 100$ mL of dichloromethane. The combined organic phases were washed twice with 20 mL of distilled water and dried over anhydrous $Na_2SO_4$. After filtration, the solvent was partly evaporated under reduced pressure and the polymer was precipitated from the resulting concentrated solution by addition of diethyl ether. The product copolymer was dried under vacuum for 24 h. $^1$H NMR ($CDCl_3$)=δ 4.06 (t, 3H, —$OCH_2$), 3.4 (m, 1H, —CH—COOH), 2.31 (t, 2H, —$CH_2$), 1.66 (m, 2H, —$CH_2$), 1.37 (m, 2H, —$CH_2$) ppm.

Example 5

Synthesis of 4% PEG-86% PCL-10% cPCL Copolymer

A reaction procedure similar to the one used in the synthesis of 90% PCL-10% cPCL described in Example 4 was used by replacing PCL with 4% PEG-96% PCL as a starting material. $^1$H NMR ($CDCl_3$)=δ 4.06 (t, 3H, —$OCH_2$), 3.4 (m, 1H, —CH—COOH), 2.31 (t, 2H, —$CH_2$), 1.66 (m, 2H, —$CH_2$), 1.37 (m, 2H, —$CH_2$) ppm.

Example 6

Synthesis of 8% PEG-82% PCL-10% cPCL copolymer

A reaction procedure similar to the one used in the synthesis of 90% PCL-10% cPCL described in Example 4 was used by replacing PCL with 8% PEG-92% PCL as a starting material. $^1$H NMR (CDCl$_3$)=δ 4.06 (t, 3H, —OCH$_2$), 3.4 (m, 1H, —CH—COOH), 2.31 (t, 2H, —CH$_2$), 1.66 (m, 2H, —CH$_2$), 1.37 (m, 2H, —CH$_2$) ppm.

Example 7

Polymer Degradation

Degradation properties of polymers were characterized by measuring M$_n$ over time (i.e., 0, 4, 7, and 28 days) after incubation of polymer samples in phosphate buffered saline (PBS) at 37° C., using GPC as described above.

TABLE 1

Polymer degradation properties

| Polymer Composition | Day 0 (kDa) | Day 4 (kDa) | Day 7 (kDa) | Day 28 (kDa) | % Mn Remaining |
|---|---|---|---|---|---|
| 100% PCL | 93.2 | 86.9 | 84.1 | 80.7 | 86.60% |
| 90% PCL-10% cPCL | 139.1 | 135.7 | 133.2 | 112.4 | 80.80% |
| 4% PEG-86% PCL-10% cPCL | 95.3 | 92.2 | 85.7 | 71.3 | 74.80% |

Results are illustrated in Table 1, where the percent remaining represents the M$_n$ at day 28 relative to the initial value. The M$_n$ of 100% PCL decreased by ~13% at 28 days post-incubation. With the addition of 10% cPCL to the PCL homopolymer (i.e., 90% PCL-10% cPCL), the polymer degraded more quickly (~19%) and this effect was enhanced (~25%) upon addition of the hydrophilic 4% PEG subunit (i.e. 4% PEG-86% PCL-10% cPCL).

Example 8

Thermal Properties

Thermogravimetric analysis (TGA-1000, Instrument Specialist Inc., Twin Lakes, Wis.) was performed using a heating rate of 20° C./minute to a final temperature of 600° C. Differential scanning calorimetry (DSC, Q1000, TA Instruments, New Castle, Del.) was performed with a sample mass of between 5 and 10 mg, in aluminum pans with tops. The procedure included two runs from −80° C. to 100° C. with a ramp rate of 10° C./minute. The values from the second run were reported such that thermal history was erased (n=3).

TGA results are illustrated in FIG. 1, and demonstrate stability of all polymers up to 200° C., supporting their use in physiological applications. DSC was then used to monitor changes in the thermal properties of different polymer composition, with results illustrated in Table 2. The enthalpy change (ΔH) and melting temperature (T$_m$) of 100% PEG were higher than those of 100% PCL. Compared to 100% PCL, ΔH and T$_m$ increased upon addition of PEG to the PCL homopolymer (i.e., 4% PEG-96% PCL and 8% PEG-92% PCL), but decreased with cPCL (i.e., 90% PCL-10% cPCL) (Table 2). Addition of both PEG and cPCL in the terpolymers (i.e., 4% PEG-86% PCL-10% cPCL and 8% PEG-82% PCL-10% cPCL) dramatically decreased ΔH and T$_m$, compared to the test homo- and copolymers. Also, ΔH and T$_m$ increased as the PEG content increased from 4% to 8% in the test terpolymers.

TABLE 2

Polymer thermal properties

| Polymer Composition | ΔH (J/g) | Tm (° C.) |
|---|---|---|
| 100% PCL | 79.24 | 58.01 |
| 90% PCL-10% cPCL | 73.68 | 57.82 |
| 4% PEG-96% PCL | 82.21 | 57.28 |
| 8% PEG-92% PCL | 91.26 | 58.06 |
| 4% PEG-86% PCL-10% cPCL | 58.12 | 57.00 |
| 8% PEG-82% PCL-10% cPCL | 70.97 | 57.14 |
| 100% PEG | 216.67 | 60.47 |

Example 9

Mechanical Properties

Dynamic mechanical analysis (DMA, Q800 DMA, TA Instruments) was performed with samples that were soaked in dH$_2$O at 37° C. for 2 days prior to testing. Wet stress and strain were recorded using a submersion clamp containing dH$_2$O at room temperature. A preload force of 0.1 N was applied to each sample and force was increased at a rate of 0.1 N/minute until failure. The average Young's Modulus was measured (n=3). For temperature sweeps, a tension clamp was used with dry samples in air. The procedure included two runs from −80° C. to 50° C. with a ramp rate of 20° C./minute and a strain of 10% at 1 Hz. All values were calculated using Universal Analysis software provided by TA Instruments.

The DMA results demonstrate that the wet glass transition temperature (Wet T$_g$) decreased as the PEG and/or the cPCL content(s) increased in the test polymer types (Table 3). In particular, in the test terpolymers, the addition of cPCL amplified the PEG effect, resulting in a further reduction of Wet T$_g$, consistent with a decrease in crystallinity. Upon addition of cPCL (i.e., 90% PCL-10% cPCL), the wet Young's modulus (E) and ultimate tensile strength (σ$_U$) decreased, compared to 100% PCL (Table 3). Addition of PEG (i.e., 4% PEG-96% PCL and 8% PEG-92% PCL) also decreased these parameters compared to 100% PCL, but to a lesser extent than 90% PCL-10% cPCL. In terpolymers, addition of both PEG and cPCL dramatically reduced E and σ$_U$ compared to the test homo- and co-polymers, indicating the combined effects of PEG and cPCL on the mechanical properties.

TABLE 3

Polymer Mechanical Properties

| Polymer Composition | Wet Tg (° C.) | Wet E (MPa) | Wet σU (MPa) |
|---|---|---|---|
| 100% PCL | −57.54 | 232.6 ± 49.6 | 14.6 ± 3.4 |
| 90% PCL-10% cPCL | −58.08 | 122.4 ± 49.4 | 7.0 ± 2.5 |
| 4% PEG-96% PCL | −57.91 | 145.6 ± 44.8 | 11.9 ± 3.3 |
| 8% PEG-92% PCL | −59.64 | 178.0 ± 47.3 | 13.0 ± 4.0 |
| 4% PEG-86% PCL-10% cPCL | −59.8 | 43.6 ± 2.9 | 2.4 ± 0.6 |
| 8% PEG-82% PCL-10% cPCL | −59.4 | 11.9 ± 4.1 | 0.6 ± 0.3 |

Example 10

Surface Chemical Properties

The sessile drop method was used to measure contact angle with an in-house goniometer. One 10 μL drop of dH$_2$O was placed on each solvent-cast film, pictures were taken immediately, and the angles on both sides of the drop were measured to represent "dry" contact angles. Samples were then incubated with dH$_2$O drops for 2 hours at 37° C. and measurements were taken to represent "wet" contact angles. All contact angles were analyzed through imaging and image analysis using ImageJ software (National Institutes of Health, Bethesda, Md.) (n=3).

Figure 2:
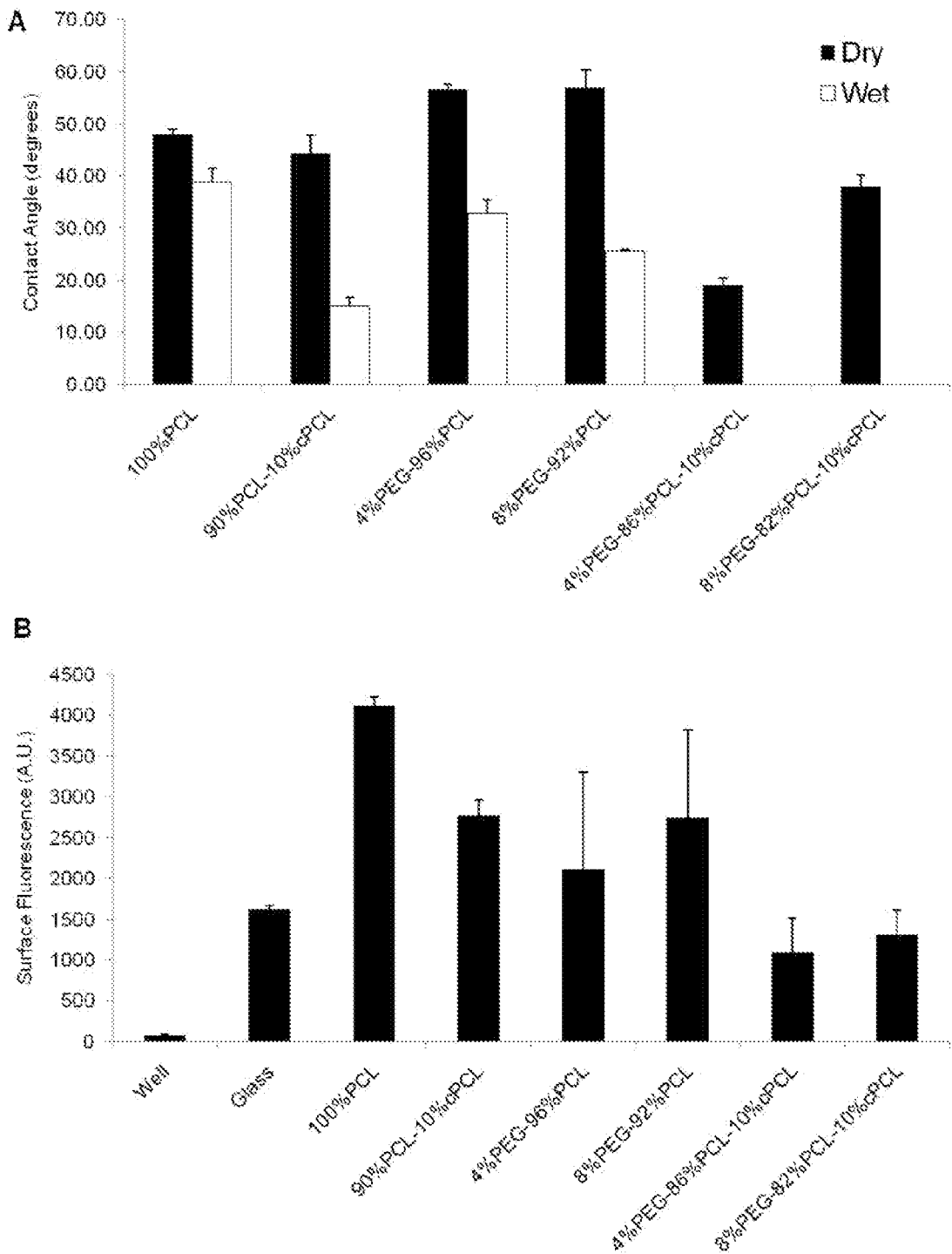
FIG. 2 is a pair of bar charts showing: (a) the results of advancing contact angle analysis of various dry and wet polymer film surfaces (n=3); and (b) the fluorescence of compositions formed by coating glass cover slips with various polymers and incubating the polymer coated cover slips with carboxylate-terminated, fluorescence-conjugated polystyrene microspheres in order to evaluate the surface chemistry of the polymers.

Results are illustrated in FIG. 2A. The "dry" sessile contact angle was not significantly different among the test polymer types. Following incubation for 2 hours at 37° C. with 95% humidity, contact angles decreased noticeably, compared to dry sessile contact angles. In particular, the "wet" contact angle decreased as the cPCL and/or PEG content increased in the test polymer types, indicating the contributions of the PEG and cPCL hydrophilic subunits. The wet contact angles were 0° on the test terpolymers, indicating that the test surfaces fully absorbed the drop.

To characterize the negative surface charge created by the carboxyl groups of cPCL, polymer-coated cover glasses were incubated with 1% v/v carboxylate-terminated, fluorescence-conjugated polystyrene microspheres (Sigma) in water overnight at 37° C. Carboxyl groups generate a negative charge on the microsphere surface and microspheres are therefore repelled more by the polymer surface as cPCL % increases. Test samples were washed three times to remove repelled microspheres from the test surfaces and the fluorescence intensity of remaining microspheres on the test sample was measured with a plate reader (infinite F500, Tecan Group Ltd., Mannedorf, Switzerland) (n=4).

Results are illustrated in FIG. 2B. The 100% PCL surface exhibited the highest fluorescence intensity, indicating the least negative charge. The addition of cPCL reduced the fluorescence intensity significantly, as compared to the test polymers that do not contain cPCL, consistent with the presence of surface charge derived from cPCL. The lowest fluorescence intensities were observed for the test terpolymers, consistent with an additional repellent effect of PEG.

Example 11

Cellular Responses in HCASMCs

To determine the optimum composition of polymers for coronary stent applications, responses of HCASMCs to test polymers were first investigated by measuring intracellular superoxide ($O_2^{\cdot-}$) and hydrogen peroxide ($H_2O_2$) in HCASMCs, as a balance of cellular oxidative mechanisms may be important for maintaining vascular homeostasis and preventing pathogenesis. Cells were incubated with dihydroethidium (DHE, Invitrogen) and dichlorofluorescein diacetate (DCFDA, Invitrogen), respectively for 30 minutes at 5 µg/mL following the previously reported method (Sung et al. *Soft Matter* 2010; 6(20):5196-5205). To measure cell viability, cells were stained with Calcein AM (1 µg/mL, Invitrogen). All cells were counterstained with Hoechst nucleus staining (5 µg/mL) to measure the total number of cells. Fluorescence intensity of each staining (i.e., DHE, DCFDA, and Calcein AM) was measured with a plate reader (Tecan) and were normalized to the corresponding cell number. To measure total protein content, cells were lysed, proteins were harvested and quantified by a colorimetric assay (BioRad, Hercules, Calif.). Cells were incubated with lipopolysaccharide (LPS, 1 µg/mL, Sigma) for one day to stimulate VCAM expression. For morphological analysis, HCASMCs were stained with Texas Red-X phalloidin (Invitrogen) and cell circularity was measured using ImageJ (n=80) (Sung et al. *Ann. Biomed. Eng.* 2005; 33(11):1546-1554). Degree of circularity is a 0-10 scale defined as 0 being an elongated morphology and 10 representing a perfect circle (circularity=$40\pi^*$(area/perimeter$^2$)).

Figure 3:
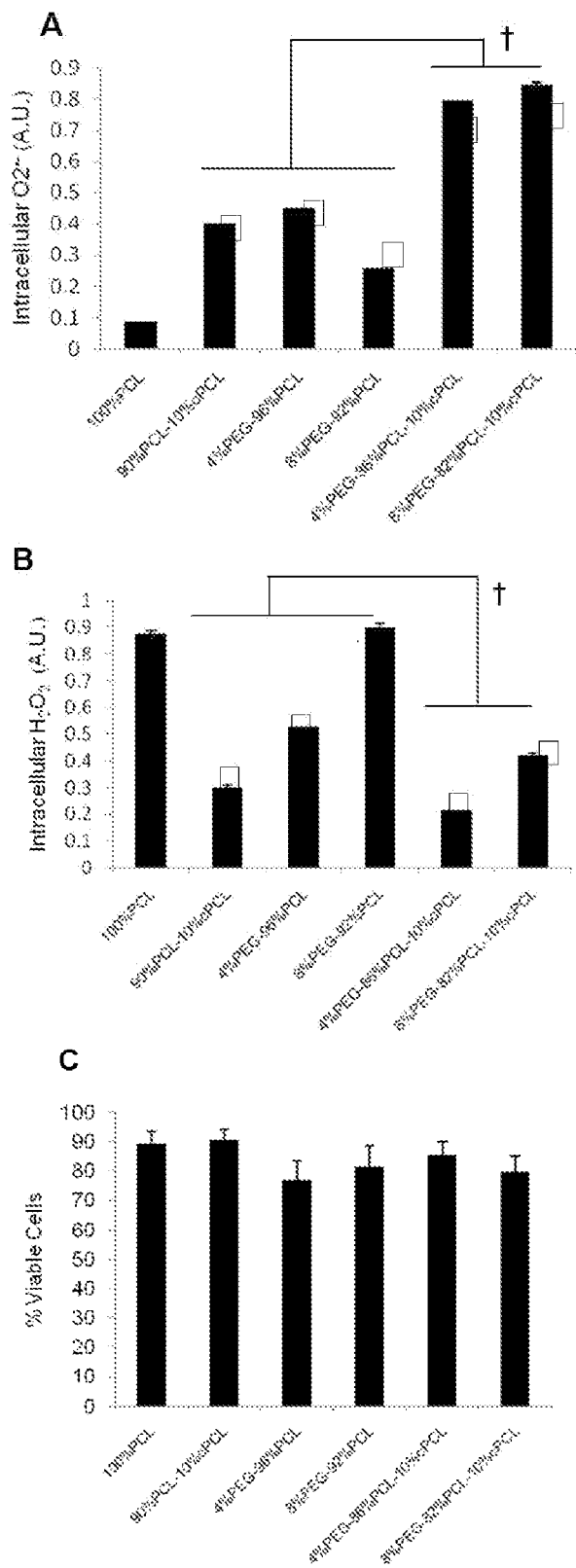
FIG. 3 is a series of bar charts showing the results of experiments to evaluate the responses of human coronary artery vascular smooth muscle cells (HCASMCs) to various polymers, including production of reactive oxygen species, cell viability and proliferation, and protein expression. The bar charts show: (a) measurements of intracellular $O_2^{\cdot-}$ determined by dihydroethidium (DHE) staining, and (b) measurements of intracellular $H_2O_2$ determined by dichlorofluorescein diacetate (DCFDA) staining (n=3 for each); (c) measurements of cell viability determined by calcein staining, and (d) measurements of proliferating HCASMCs determined by BrdU staining (n=6-12 for each); and (e) measurements of the total content of intracellular proteins and (0 measurements of smooth muscle myosin heavy chain (sm-MHC) expression (n=16-30). *p<0.01 vs. 100% PCL; †p<0.05 and ‡p<0.01 between test materials indicated by the lines.
Figure 3:
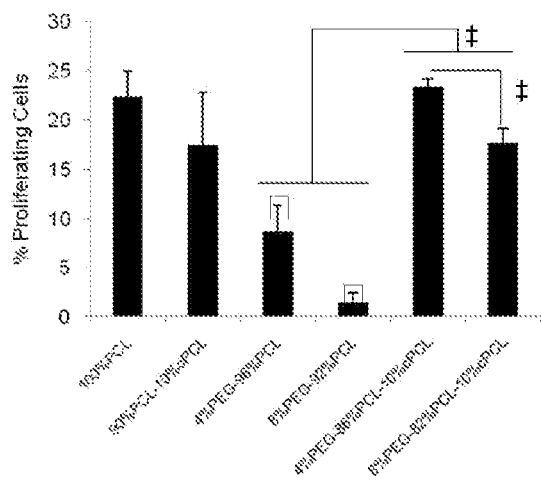
Figure 3:
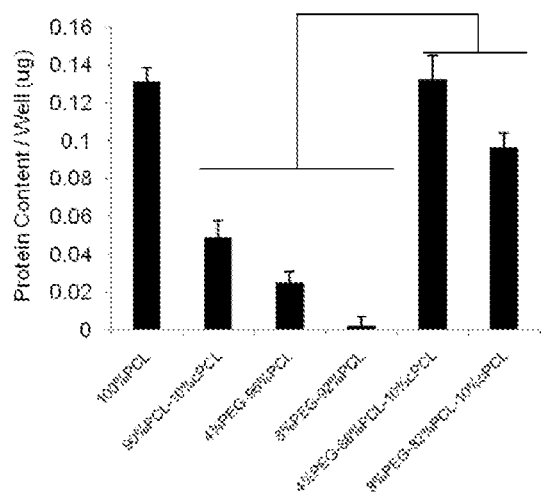
Figure 3:
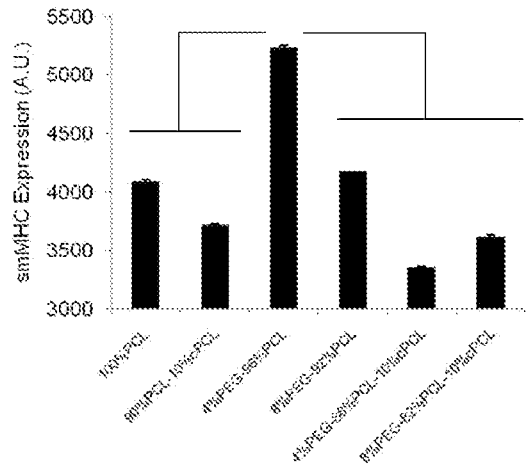

Superoxide and hydrogen peroxide varied significantly between test polymer types, as illustrated in FIGS. 3A and 3B. Intracellular $O_2^{\cdot-}$ levels correlated inversely with intracellular $H_2O_2$ levels except in the case of 4% PEG-96% PCL (FIG. 3A). For example, 8% PEG-92% PCL displayed a low level of $O_2^{\cdot-}$, but a high level of $H_2O_2$; conversely, terpolymer test samples displayed the highest levels of $O_2^{\cdot-}$ and the lowest levels of $H_2O_2$. In the test co- and terpolymers, increasing PEG molar ratios resulted in higher intracellular $H_2O_2$ levels, but this effect was counteracted by the addition of negatively-charged cPCL (FIG. 3B). HCASMCs grown on the test terpolymers showed statistically significant differences in both $H_2O_2$ and $O_2^{\cdot-}$ levels relative to other test copolymers (p<0.05).

HCAMSCs in all polymer groups maintained viability (>70%), but proliferation varied significantly (FIGS. 3C and 3D). Percentages of proliferating HCASMCs correlated proportionally with total protein content for each group (FIGS. 3D and 3E), indicating that protein synthesis is required for cells to proliferate. Cells grown on terpolymers resulted in significantly different percentages of proliferation and total protein content (p<0.05). Interestingly, proliferation percentages correlated inversely with intracellular $H_2O_2$ levels except in the case of 100% PCL (FIG. 3A).

Figure 4A:
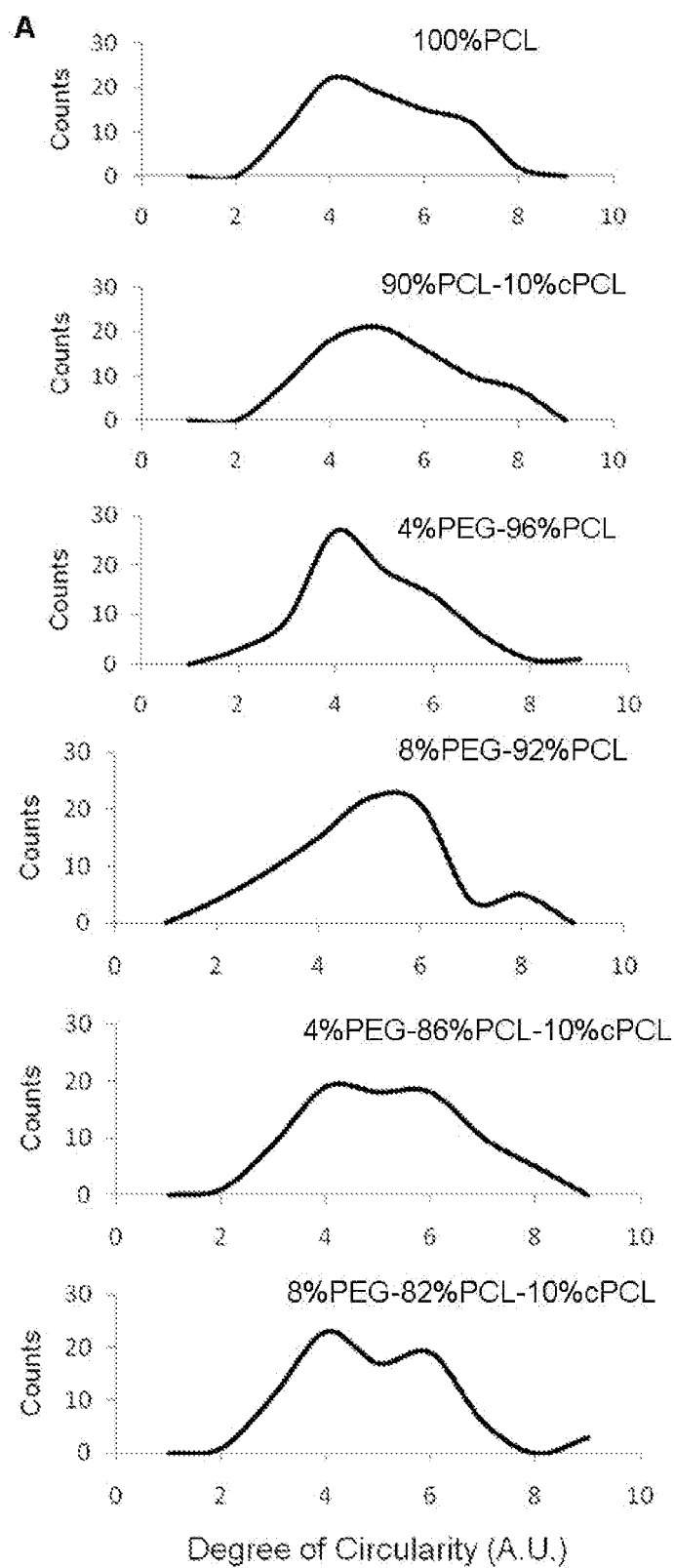
FIG. 4 depicts: (a) a series of histograms illustrating circularity distribution for HCASMCs grown on test substrates (n=80); and (b) a series of fluorescence images of HCASMCs stained with Texas Red-X phalloidin and Hoechst on four different polymer types, where the scale bars=100 μm. The bright spots in each cell represent the blue Hoechst stained-nuclei, while the remainder of the cells are stained red with Texas Red-X phalloidin, which binds to F-actin.

Staining for smMHC revealed that 4% PEG-96% PCL promoted a statistically greater level of smMHC expression in HCASMCs relative to all other conditions (p<0.01, FIG. 3F). Additionally, HCASMCs morphology was altered depending upon substrate composition (FIG. 4A). 100% PCL and 90% PCL-10% cPCL showed a slight trend towards a less circular morphology distribution. 4% PEG-96% PCL showed the most distinct peak for a low degree of circularity of all groups, supporting the highest smMHC expression of HCASMCs on this polymer. In contrast, 8% PEG-92% PCL showed the most distinct peak at a high degree of circularity. The test substrates containing PEG without cPCL resulted in the two strongest morphological biases of all polymers tested, which may be due to the ability of PEG to modulate protein adsorption and cell adhesion. The test terpolymers showed bimodal circularity distributions that represent the contributions from all three polymeric subunits: 100% PCL promotes slightly elongated morphologies, 90% PCL-10% cPCL promotes an even distribution of centered morphologies (degree of circularity ~5), and PEG-containing copolymers bias the cell morphology depending upon molar percentage (FIG. 4A).

Figure 4B:
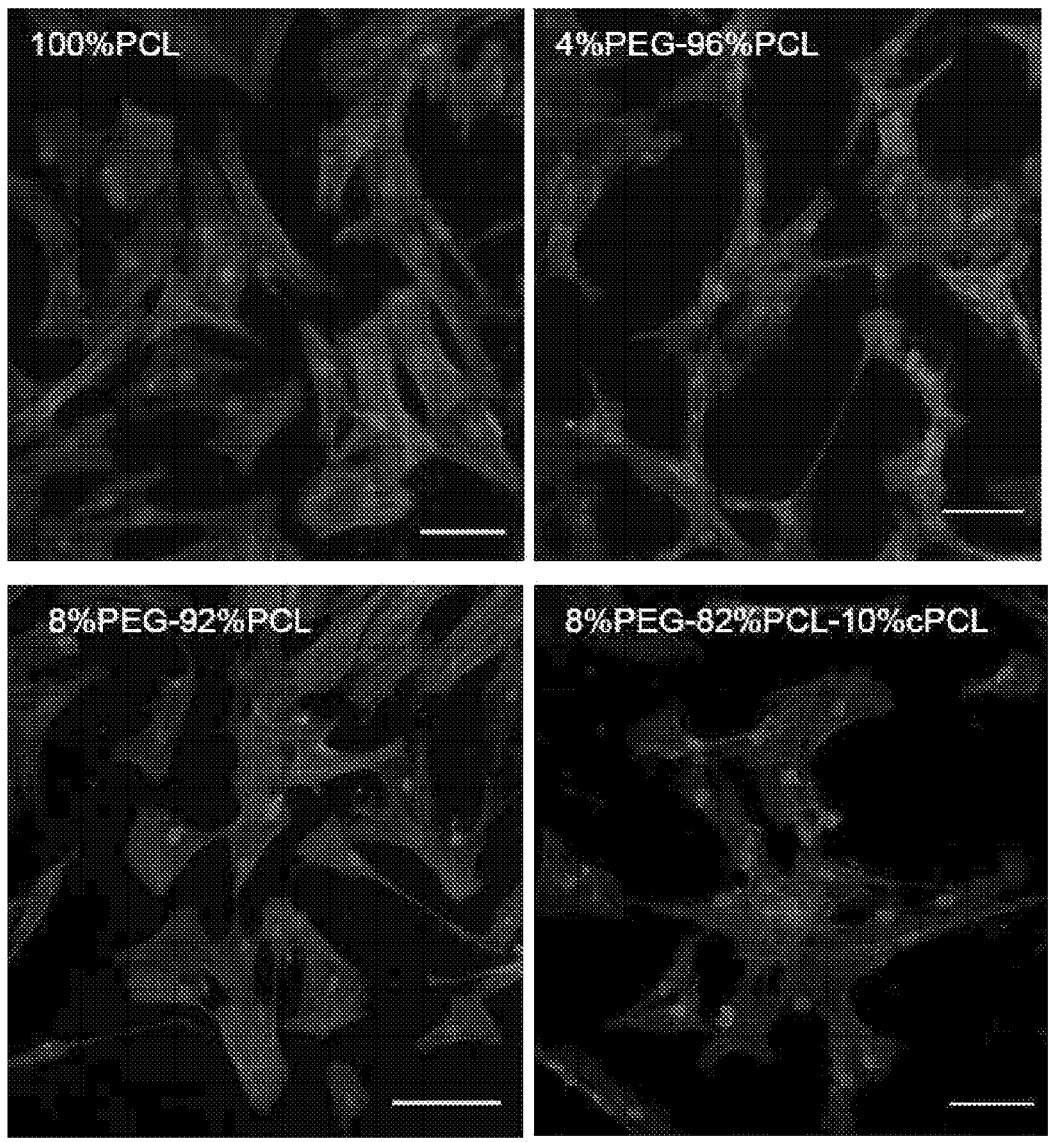

Morphological analysis revealed that cells on 4% PEG-96% PCL showed the strongest bias towards an elongated spindle-like morphology, which is a typical phenotype of healthy HCASMCs (FIG. 4B).

Example 12

Cellular Responses in HCAECs

Figure 5:
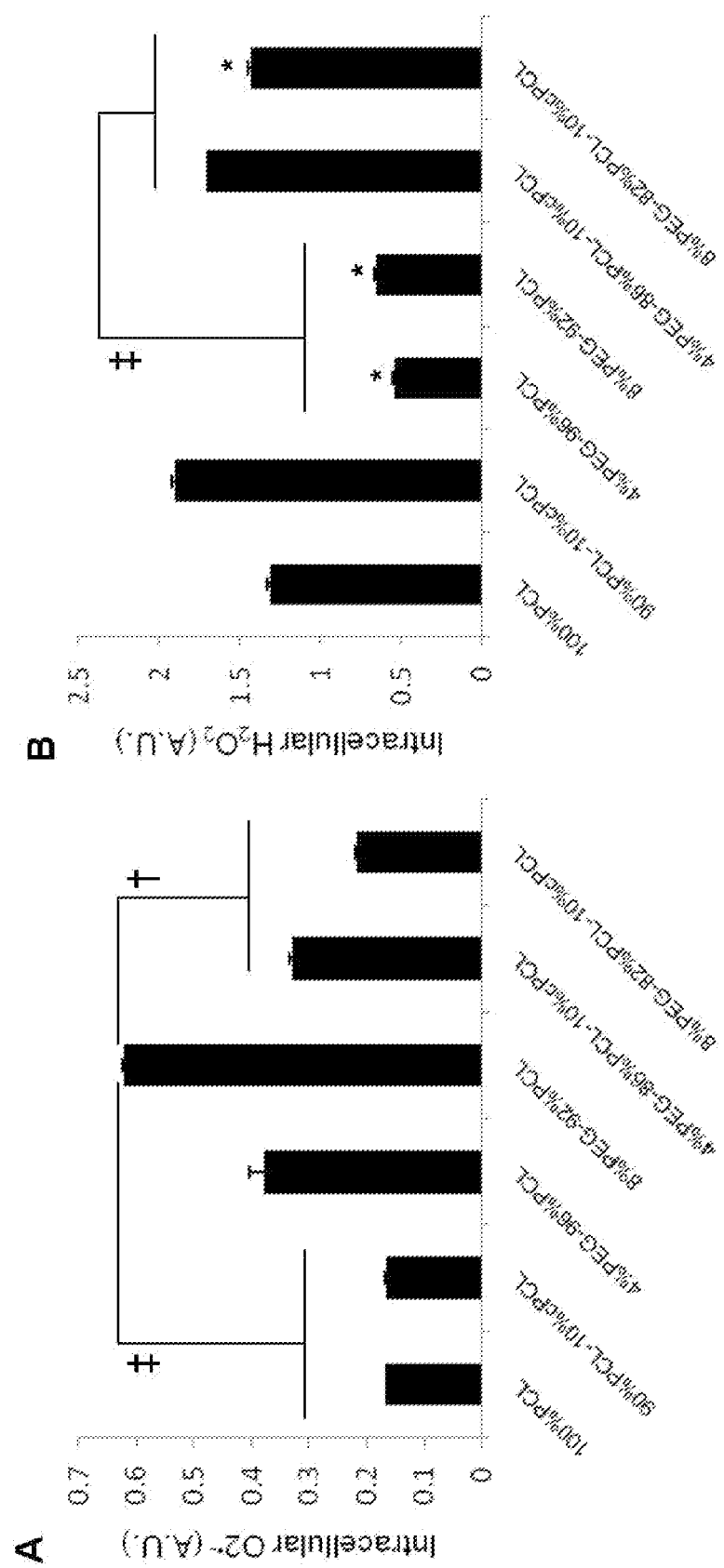
FIG. 5 is a series of bar charts showing the results of experiments to evaluate the responses of human coronary artery endothelial cells (HCAECs) to various polymers, including production of reactive oxygen species, cell proliferation, and protein expression. The bar charts show: (a) measurements of intracellular $O_2^{\cdot-}$ measured by DHE staining, and (b) measurements of intracellular $H_2O_2$ determined by DCFDA staining (n=3 for each); (c) measurements of percent proliferating HCAECs determined by BrdU staining (n=8-12); (d) measurements of vascular cell adhesion molecule (VCAM) expression (n=4). *p<0.01 vs. 100% PCL, †p<0.05 and ‡p<0.01 between test materials indicated by the lines.
Figure 5:
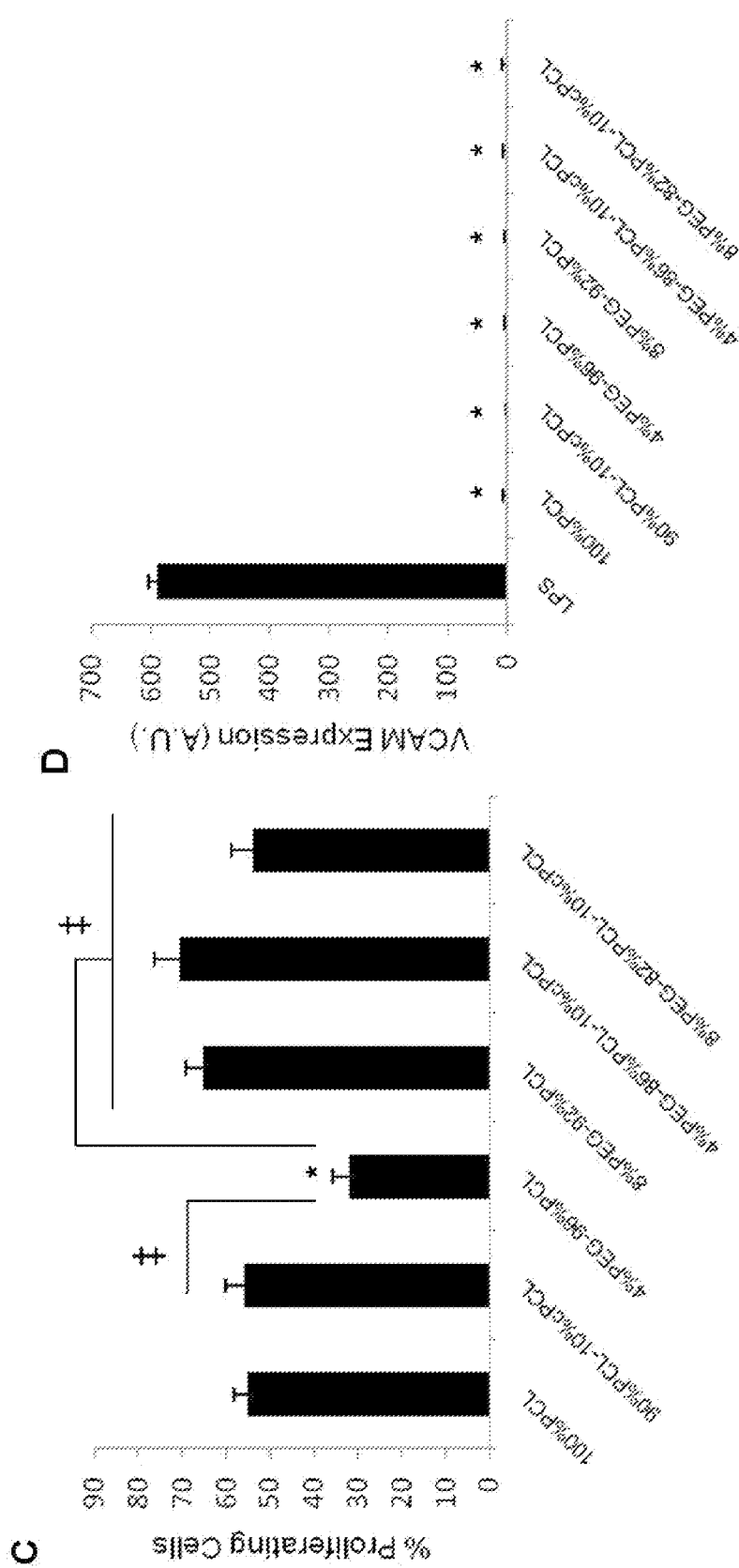

Trends in ROS levels of HCAECs were opposite to those of HCASMCs (FIG. 5A). HCAECs on the 8% PEG-92% PCL copolymer exhibited a statistically higher level of $O_2^{\cdot-}$ expression relative to all other groups except 4% PEG-96% PCL (p<0.01, FIG. 5A). Intracellular $H_2O_2$ levels of HCAECs correlated inversely with $O_2^{\cdot-}$ (FIG. 5B), which was similar to the trends seen in HCASMCs (FIGS. 3A and 3B), which may be due to the activity of superoxide dismutase. HCAECs proliferation was high (>50%) in all groups except 4% PEG-96% PCL (20-30%), which was significantly lower than 100% PCL (p<0.01) and all other groups (p<0.05, FIG. 5C). To evaluate if any of the polymers stimulate pro-inflammatory activation of HCAECs, VCAM-1 expression of HCAECs was measured on test polymers. The condition with lipopolysaccharide (LPS) treatment was used as a control (FIG. 5D). None of the polymers stimulated significant VCAM expression, thereby further supporting their applicability as biocompatible cardiovascular biomaterials, in particular as vascular stent materials.

Example 13

Electrospinning and Scanning Electron Microscopy

Polymer samples were prepared as described above in Examples 2-6. Characterization of the resulting polymers by GPC revealed that the $M_n$ ranged from 59-125 kDa, relative to monodisperse PMMA standards (Table 4).

For electrospinning, a polymer solution (10 wt %) in a mixture of chloroform and methanol (4:1 by volume) was loaded into a plastic syringe (10 ml) fitted with a stainless steel needle. This needle was connected to a high-voltage power supply. The solution was continuously supplied using a syringe pump at a rate of 1 ml/h for 10 minutes (e.g., high fiber density meshes). The voltage used for electrospinning was 18 kV and the collection distance was 10 cm. The resulting fibers were collected over glass cover slips placed on a rotating mandrel at 1200 rpm. The scaffolds were dried under vacuum for 24 h and sterilized by UV irradiation for 30 minutes before cell culture.

To reduce the modulus of electrospun fibers (e.g. low fiber density meshes), the flow rate of polymer solution was reduced from 1 ml/h to 0.25 ml/h while keeping the other conditions the same. The fibers were collected over an aluminum woven wire mesh with a wire diameter of 1.0 mm, a wire spacing of 0.381 mm, and a dimension of 25 mm (L)×10 mm (W) (McMaster-Carr Co., Robbinsville N.J., USA).

For SEM imaging, electrospun scaffolds were coated with gold using a sputter coater (Cressington Scientific, Watford, United Kingdom) and fiber structures were examined using SEM (Hitachi S-4200, Tokyo, Japan) at an accelerating voltage of 5 kV.

Dry elastic moduli of electrospun polymer scaffolds were determined using a tabletop uniaxial testing machine (Bose ElectroForce 3100, Eden Prairie, MN) using a 10-N load cell under a cross-head speed of 10 mm/min in ambient conditions (n=3~6). Scaffold samples were prepared in a uniform rectangular form. The thicknesses of test specimens were 0.1 mm as measured using digital calipers.

Wet elastic moduli of electrospun polymer scaffolds were measured by dynamic mechanical analysis (DMA, Q800 DMA, TA Instruments, New Castle, Del.) (n=3). Scaffold samples were prepared in a uniform rectangular form with the dimension of 15.0 (l)×6.6 (w) mm². A wet et stress and strain curve was obtained using a submersion clamp containing water at room temperature. A preload force of 0.1 N was applied to each sample and force was increased at a rate of 0.1 N/min until failure.

Dry and wet elastic moduli for the electrospun polymer scaffolds are illustrated in Table 4. The polymers exhibited dry elastic moduli from 7.58 to 23.21 MPa. Among all polymer scaffolds tested, PCL exhibited the lowest elastic modulus (7.58 MPa), whereas the stiffest material was the 4% PEG-86% PCL-10% cPCL terpolymer (23.21 MPa). Following hydration to equilibrium, PEG- and cPCL-containing polymers exhibited a greater decrease in wet elastic modulus compared to PCL. This phenomenon may be explained by taking into account the hydrophilicity of the polymer subunits. Since cPCL and PEG monomers are hydrophilic, segments containing these moieties were expected to become less rigid upon hydration, causing the wet elastic modulus of the system to be lower than the dry modulus. While a decrease in wet relative to dry elastic moduli was also observed for PCL, this could be explained by water retention by these fibrous scaffolds rather than dissolution of polymer fibers.

TABLE 4

Polymer properties and mechanical properties of electrospun polymers

| Polymer | $M_n^a$ (Da) | PDI | Dry modulus[b] (MPa) | Wet modulus[c] (MPa) |
|---|---|---|---|---|
| PCL | 91,720 | 1.25 | 7.58 | 0.79 |
| 4% PEG-96% PCL | 93,070 | 1.24 | 21.29 | 0.81 |
| 8% PEG-92% PCL | 104,200 | 1.21 | 15.40 | 0.74 |
| 90% PCL-10% CPCL | 112,800 | 1.06 | 13.33 | 0.98 |
| 4% PEG-86% PCL-10% CPCL | 108,400 | 1.16 | 18.11 | 0.71 |
| 8% PEG-82% PCL-10% CPCL | 65,350 | 1.27 | 23.21 | 0.81 |

[a]Molecular weight measured by GPC in THF,
[b]Measured on a uniaxial Bose ElectroForce 3100 mechanical tester,
[c]Measured by DMA Example 14

Intracellular Reactive Oxygen Species (ROS) and Cell Viability

For these cell assays, mouse germ line competent CGR8 embryonic stem cells were used as described in the Materials & Methods section. Embryoid bodies (EBs) were formed at day 0 by inverting droplets consisting of 25 cells/µl in media without LIF. At day 2, the EBs were transferred from this hanging drop culture into Petri dishes. For high fiber density substrates, EBs were moved at day 4 to electrospun polymer scaffolds coated with 0.1% gelatin on glass coverslips in tissue culture plates. For low fiber density substrates, fiber meshes were immobilized to the membrane side of a modified transwell insert after removing an insert membrane. Following day 10, in vitro measurements were performed upon visual confirmation of the presence of beating EBs.

Beating, α-MHC-DsRed-transfected CGR8 cells at day 10 were analyzed for intracellular ROS production and cell viability. Intracellular hydrogen peroxide production was measured using dichlorofluorescein diacetate (DCFDA, Invitrogen) following the manufacturer's instructions. Cell viability was measured using calcein AM (Invitrogen). The fluorescence intensity was measured on a Tecan infinite F500 plate reader (Mannedorf, Switzerland) and normalized to the corresponding cell number measured from Hoechst nuclear staining.

Figure 6:
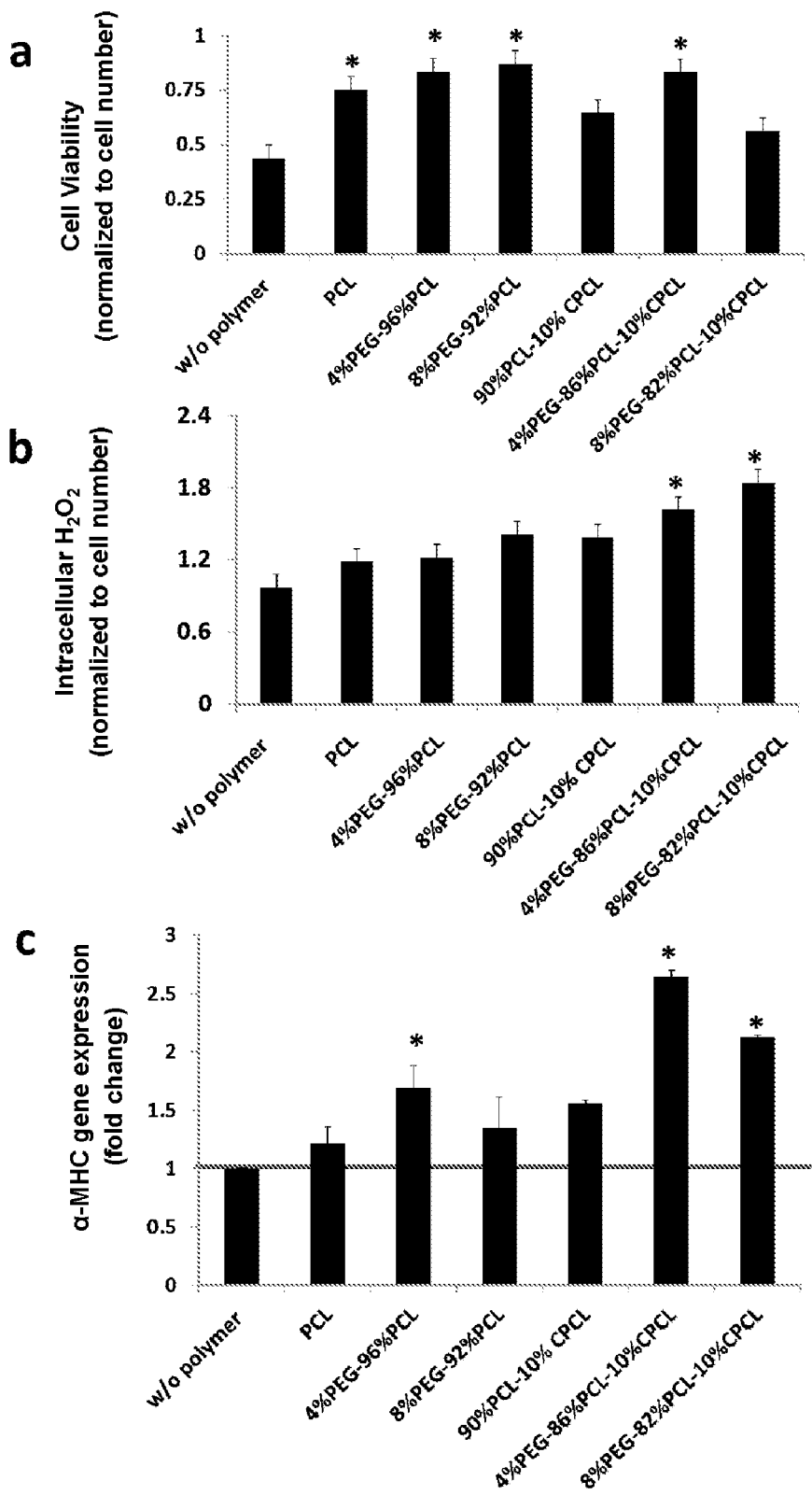
FIG. 6 is a series of bar charts showing the results of experiments to evaluate the reactions of embryoid bodies (EBs) to growth on various polymer scaffolds. The bar charts show: (a) measurements of cell viability determined by calcein staining; (b) measurements of intracellular $H_2O_2$ determined by DCFDA staining; (c) measurements of α-myosin heavy chain (α-MHC) gene expression determined using the real-time polymerase chain reaction (RT-PCR). In each case, the data represents the mean±standard deviation. Statistical significance in relation to growth of EBs without polymer scaffolds at the p<0.05 level is shown by the *.

ESCs on all test polymer types showed higher cell viability compared to control (glass coverslip without polymer, FIG. 6a). In particular, PCL, 4% PEG-96% PCL, 8% PEG-92% PCL and 4% PEG-86% PCL-10% cPCL exhibited the most significant enhancement in cell viability. Since low levels of intracellular ROS have been implicated in ESC differentiation towards both cardiomyogenic and vascular cell lineages (Sauer et al. *Antiox. Redox Sign.* 2005; 7(11-12):1423-1434), intracellular hydrogen peroxide ($H_2O_2$) levels were measured. Test polymer types differentially regulated intracellular $H_2O_2$ production (FIG. 6b). In particular, the terpolymer types (i.e., 4% PEG-86% PCL-10% cPCL and 8% PEG-82% PCL-10% cPCL) enhanced intracellular $H_2O_2$ most significantly.

Figure 7:
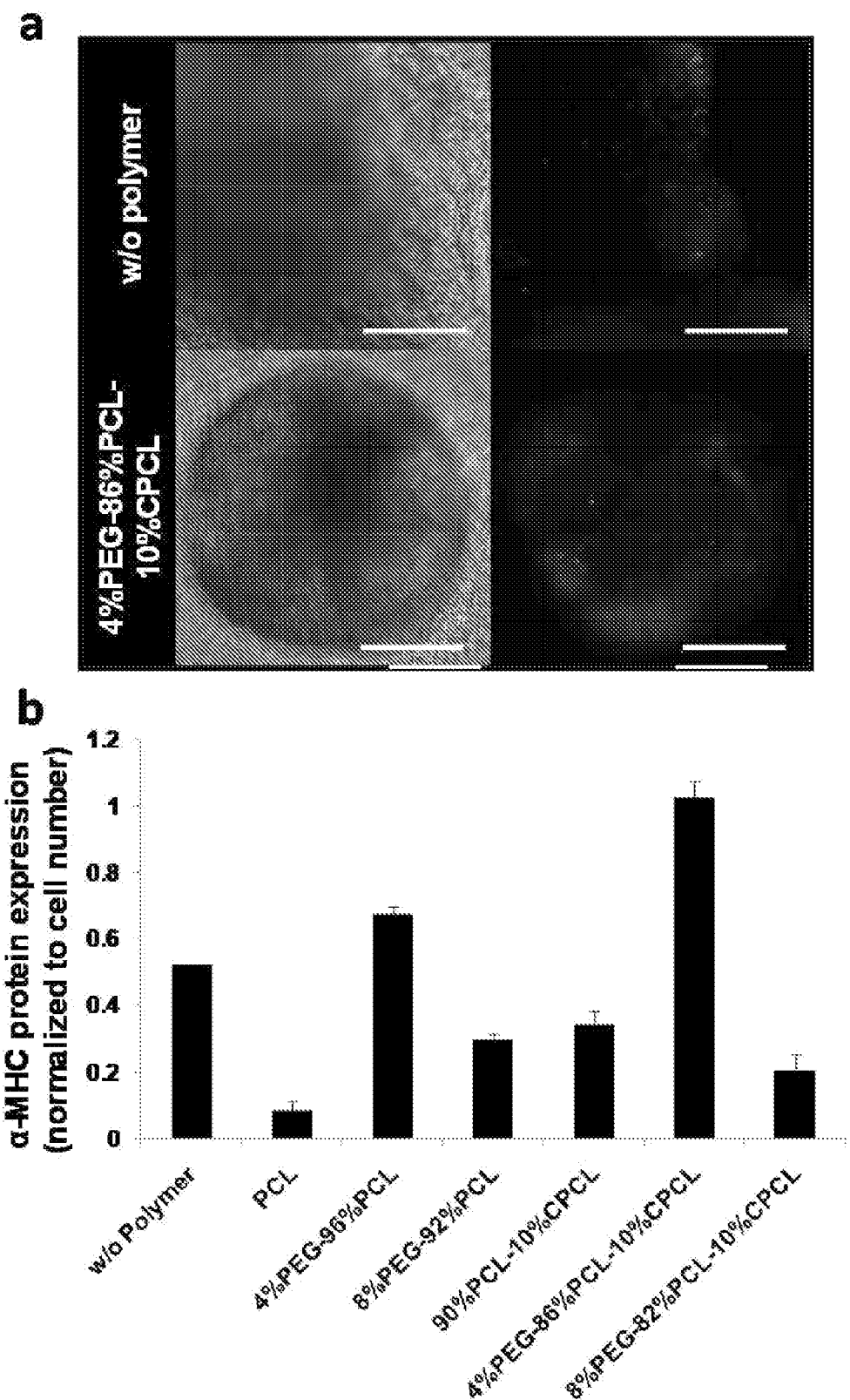
FIG. 7 illustrates the results of experiments evaluating the interaction of EBs with various polymers. (a) Phase contrast and fluorescence images of EBs at day 10 of growth on gelatin coated glass cover slips with and without 4% PEG-86% PCL-10% cPCL copolymer scaffolds. (Bars represent 10 um); (b) a bar chart showing the results of experiments to determine α-MHC protein expression in EBs grown on various polymers.

To further quantify the differentiation of ESCs to cardiomyocytes, gene expression of α-MHC (a marker of cardiac lineage) was measured via real time PCR (FIG. 6c). ESCs on all the test polymer types up-regulated α-MHC gene expression compared to control. ESCs grown on terpolymer fiber scaffolds (i.e., 4% PEG-86% PCL-10% cPCL and 8% PEG-82% PCL-10% cPCL) exhibited the greatest increase in α-MHC gene expression (~2-fold relative to control). To further confirm α-MHC expression at a protein level, transfected ESCs on fiber scaffolds were imaged and α-MHC fluorescence intensity was quantified through image analysis (FIG. 7). Representative phase contrast and fluorescence images demonstrated improved attachment of EBs on 4% PEG-86% PCL-10% cPCL relative to control (FIG. 7a). EBs on the 4% PEG-86% PCL-10% cPCL scaffolds also exhibited faster beating rates compared to control (data not shown). Interestingly, the level of α-MHC protein expression in EBs was dependent on the polymer composition (FIG. 7b). EBs cultured on 4% PEG-96% PCL and 4% PEG-86% PCL-10% cPCL scaffolds exhibited up-regulated α-MHC expression relative to control whereas protein expression was substantially down-regulated in the other test polymer groups.

Taken together, 4% PEG-86% PCL-10% cPCL was found to be the most favorable polymer composition for maintaining EB viability and enhancing their differentiation to cardiomyocytes, whereas 100% PCL was found to be the least favorable composition for the tested cellular functions.

Example 15

Effects of Scaffold Mechanical Properties on ESC Differentiation

In addition to the fibrous scaffolds made by electrospinning with a flow rate of 1 ml/h for 10 min as described in Example 13, a second set of scaffolds was prepared by reducing the flow rate (0.25 ml/h) and doubling the deposition time (20 min) to reduce fiber density. Due to the resulting scaffold morphology determined by SEM, these two scaffold types will be referred to as "high-" (FIG. 8a) and "low-" (FIG. 8b) fiber density scaffolds, respectively.

Figure 8:
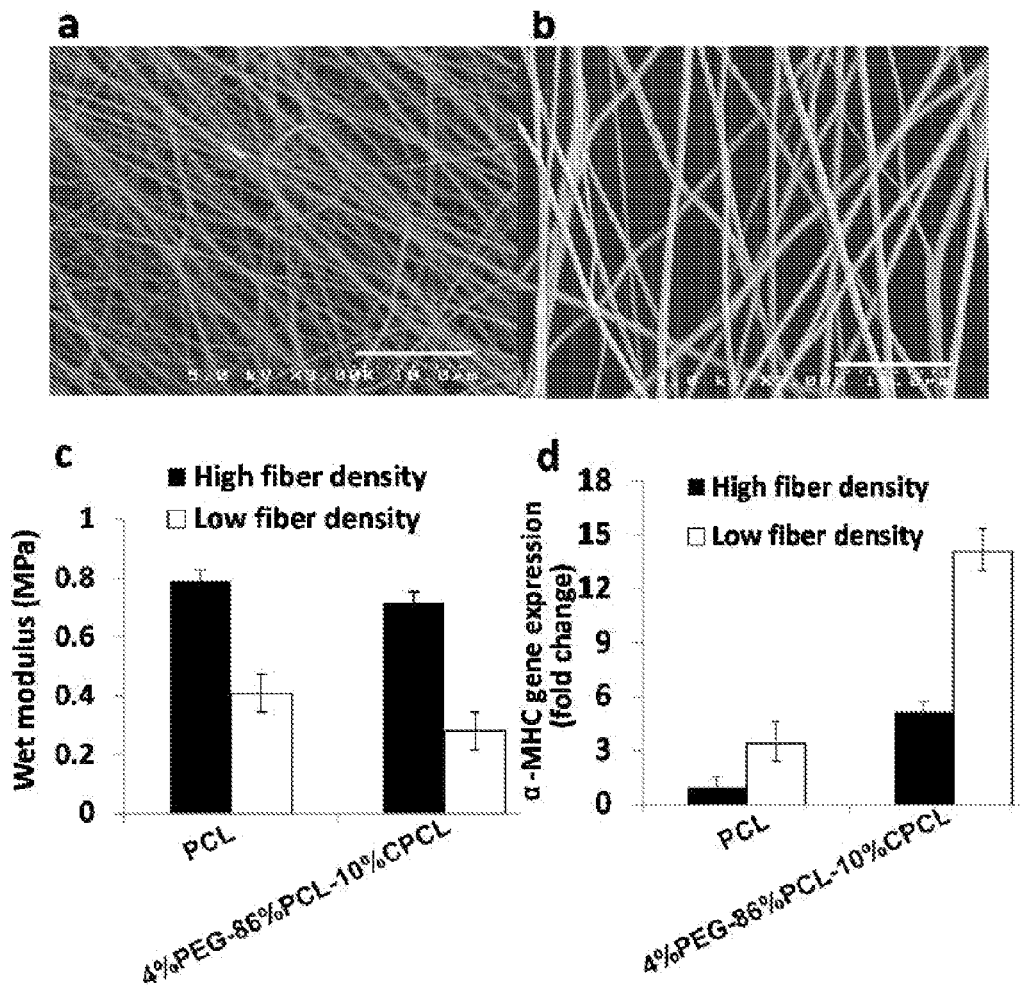
FIG. 8 illustrates the results of experiments evaluating various electrospun polymer scaffolds. Shown are SEM images of: (a) high-density 4% PEG-86% PCL-10% cPCL polymer scaffold and (b) low-density 4% PEG-86% PCL-10% cPCL polymer scaffold; (c) a bar chart showing the results of experiments to measure the wet modulus of high- and low-density PCL and 4% PEG-86% PCL-10% cPCL polymer scaffolds; and (d) a bar chart showing the results of experiments to measure α-MHC gene expression in EBs grown on high- and low-density PCL and 4% PEG-86% PCL-10% cPCL polymer scaffolds, determined by RT-PCR measurement. Data represents mean±standard deviation. Statistical significance in relation to without polymer scaffolds at the p<0.05 level is shown by the *.

Fiber density in the scaffolds positively correlated with the wet elastic moduli inversely (FIG. 8c). PCL scaffolds with high- and low-fiber densities exhibited wet moduli of 0.79 MPa and 0.42 MPa, respectively, whereas 4% PEG-86% PCL-10% cPCL scaffolds possessed similar but slightly lower moduli of 0.71 and 0.28 MPa, respectively. This may be because the hydrophilicity of PEG and cPCL in 4% PEG-86% PCL-10% cPCL increased hydration and water retention relative to the hydrophobic PCL only. In consequence, polymer chains within the terpolymer scaffolds may be better hydrated and separate more freely in an aqueous environment, leading to lower moduli.

To evaluate effects of fiber density on EB differentiation at the gene level, non-transfected EBs were cultured on four scaffold types immobilized to the membrane side of the membrane-free transwell insert and α-MHC expression was measured by RT-PCR. Cardiomyogenic differentiation of EBs was shown to be significantly influenced by scaffold mechanical properties (FIG. 8d). For both polymer types tested, low-fiber density scaffolds with decreased moduli promoted higher α-MHC gene expression than high-fiber density scaffolds (2-fold higher for PCL, ~3-4-fold higher for 4% PEG-86% PCL-10% cPCL). These results indicate that substrate mechanical properties, in addition to chemical properties, may play an important role in promoting differentiation of EBs into cardiomyocytes.

Example 16

Calcium Ion Dynamics $Ca^{2+}$ signaling may play an essential role in cardiac excitation and contraction. To further validate the ability of fiber mesh scaffolds to enhance differentiation of EBs into cardiomyocytes, $Ca^{2+}$ transients were recorded from isolated EBs that had been removed from high fiber density 4% PEG-86% PCL-10% cPCL fiber scaffolds deposited on coverglass templates compared to the results from controls with coverglasses only without polymers. Also the same $Ca^{2+}$ transient parameters were compared in low fiber density 4% PEG-86% PCL-10% cPCL versus PCL only. Because low fiber density scaffolds were shown to enhance α-MHC expression compared to high fiber density substrates, the two polymer types were compared in a low fiber density format. Again, low fiber density scaffolds were immobilized to transwell inserts (see Example 13; high fiber density meshes were deposited directly onto glass cover slips, but low fiber density meshes were immobilized to the membrane side of a "membrane-free" modified transwell insert). Because of this, differences in calcium dynamics between low and high fiber density samples could not be directly compared, but rather insight based upon changes within each group were examined EBs were detached from the polymer substrates and re-suspended in 2 ml media. The EBs were loaded with 5 mM Fura-2 AM (Invitrogen, CA) for 15 minutes before centrifugation and resuspension in fresh, dye-free media for 15 minutes to allow for deesterification of the AM dye before recording of $Ca^{2+}$ signaling spikes. Each EB was field-stimulated at 1 Hz in a custom built imaging dish using platinum wire electrodes. Excitation light was multiplexed at wavelengths of 360 nm and 380 nm using a computer controlled monochromator (Cairn, UK). Resulting fluorescence was recorded at a wavelength of 510±20 nm using an array of optical fibers coupled to photomultiplier tubes (Hamamatsu Photonics, Shizuoka, Japan) positioned in the focal plane of a Zeiss Axiovert 200 microscope (Oberkochen, Germany) Recordings were taken at multiple sites on each EB. The fluorescence ratios (I@360 nm/I@380 nm) were postprocessed with a 200 Hz low-pass filter. The transient amplitude is the difference between the systolic and diastolic fluorescence ratios. The decay constant was computed by fitting a single exponential decay starting from the maximum fluorescence ratio using Origin (OriginLab, MA).

Figure 9:
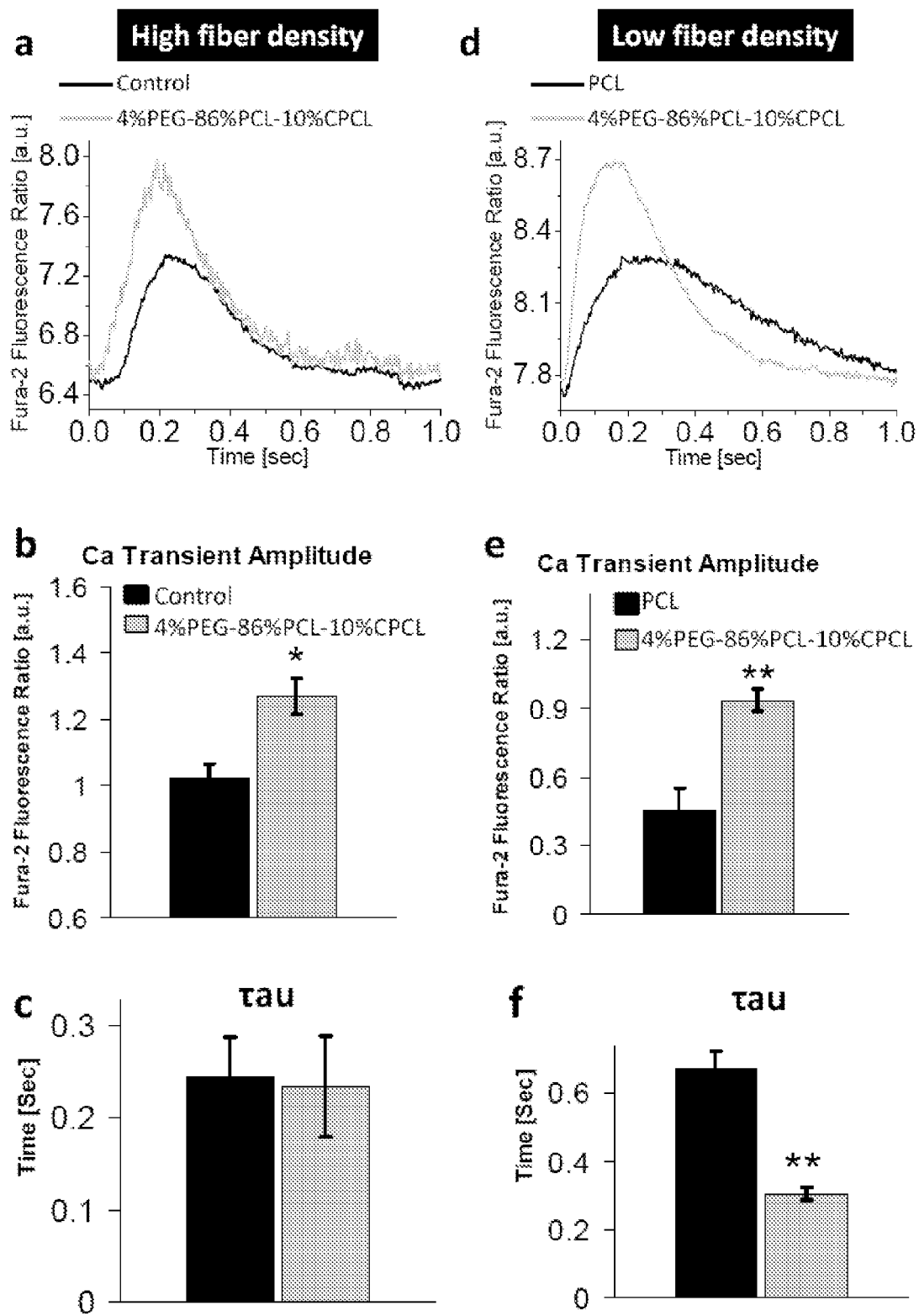
FIG. 9 illustrates the results of experiments to determine how polymer substrate elasticity affects $Ca^{2+}$ dynamics in isolated EBs. $Ca^{2+}$ transients were recorded from isolated EBs using ratios of Fura-2 fluorescence. The EBs were subjected to 1 Hz field-stimulation during recordings. Experiments were performed on both high-density (a, b and c) and low-density (d, e and f) polymer scaffolds of either 100% PCL or 4% PEG-86% PCL-10% cPCL. (a) and (d) illustrate representative fluorescence traces showing calcium transients accompanying a single beat. (b) and (e) show $Ca^{2+}$ transient amplitudes, measured as the difference between diastolic and systolic Ca fluorescence intensities. (c) and (f) show decay constants of the $Ca^{2+}$ transients, calculated by fitting the decay to a single exponential decay function.

Results are illustrated in FIG. 9. For measurements of calcium dynamics, the ratio of the fluorescence emission intensities of the Fura-2 fluorophore at 360 and 380 nm can be directly correlated to intracellular $Ca^{2+}$. The EBs were subjected to 1 Hz field-stimulation during recordings. By recording fluorescence ratios over time, calcium transients resulting from a single field stimulus were observed. High fiber density 4% PEG-86% PCL-10% cPCL meshes were shown to promote a stronger $Ca^{2+}$ ion transit intensity when compared to control (glass only, FIG. 9a), and low fiber density 4% PEG-86% PCL-10% cPCL meshes promoted a stronger $Ca^{2+}$ ion transit intensity when compared to PCL (FIG. 9d). Regardless of polymer composition, low fiber density substrates were shown to enhance $Ca^{2+}$ ion transit intensity more effectively than high fiber density 4% PEG-86% PCL-10% cPCL, indicating the strong influence of fiber density and the resulting mechanical properties on cardiomyogenic differentiation.

For both low and high fiber density substrates, 4% PEG-86% PCL-10% cPCL fiber meshes promoted better differentiation toward cardiomyocytes than PCL only or glass control, respectively. This was evidenced by higher calcium transient amplitudes that indicates the difference between systolic and diastolic [$Ca^{2+}$] (FIGS. 9b and e), as well as lower tau values (relaxation time constant, FIGS. 9c and f). These data suggest that the EBs isolated from the terpolymer scaffolds may possess a propensity for faster depolarization-repolarization cycles, indicating superior cardiac function.

Example 17

Bone Morphogenic Protein (BMP) Inhibitor and Immunohistochemistry

To promote cardiomyogenic differentiation of cells, dorsomorphin, a small molecule inhibitor of BMP signaling, was added to EBs Inhibition of BMP pathways in ESCs can lead to at least a 20-fold enhancement in cardiomyogenic differentiation of ESCs (Hao et al. *PLoS ONE* 2008; 3(8):e2904). At day 4, EBs were fixed with 2% paraformaldehyde and permeabilized with 0.2% Triton X-100. Cells were blocked with 5% bovine serum albumin in PBS for 30 min at 37° C. Cells were then incubated with Rabbit anti-mouse SERCA2a (Sarcoplasmic Reticulum $Ca^{2+}$ ATPase isoform 2a) IgG antibody (provided by Dr. Björn Knollmann at Vanderbilt University Medical Center) in 1:1000 dilution with 5% bovine serum albumin in PBS for 1.5 h at 37° C., followed by incubation with secondary FITC-conjugated goat anti-rabbit IgG antibodies (Sigma-Aldrich). The cells were imaged under a Nikon Eclipse Ti inverted fluorescence microscope (Nikon Instruments Inc, Melville, N.Y.).

Figure 10:
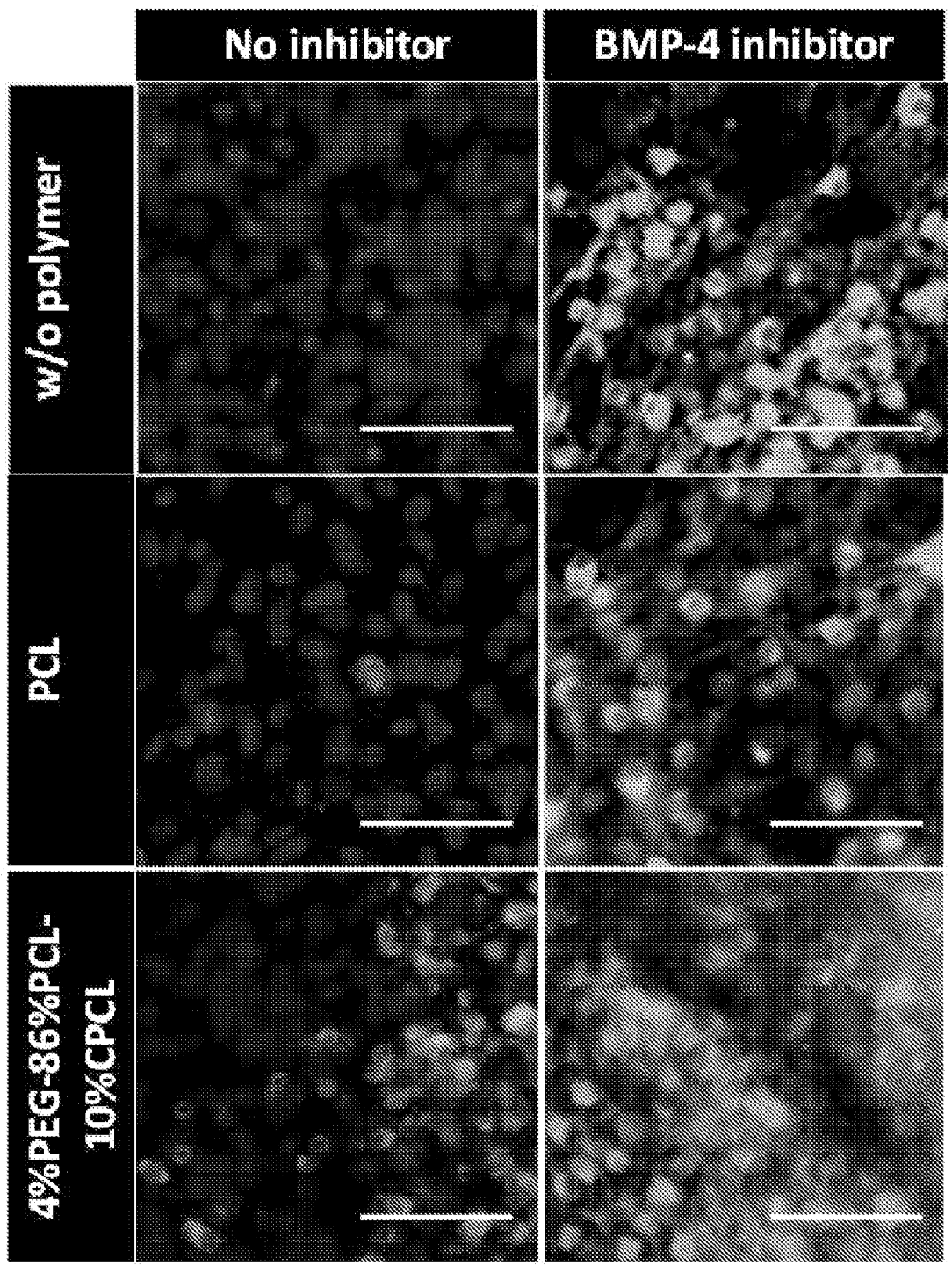
FIG. 10 depicts a series of fluorescence images of EBs grown on various polymers, with and without dorsomorphine (BMP-4 inhibitor) treatment, stained with mouse anti-SERCA 2a primary antibody. SERCA2a was detected using FITC-conjugated anti-rabbit IgG secondary antibody. The scale bar is 50 um.

As shown in FIG. 10, ESCs were stained for SERCA2 (green), a marker of cardiac differentiation, and counterstained with Hoechst (blue) in order to further visualize and validate differentiation to cardiomyocytes. In the absence of dorsomorphin, SERCA2 expression was low and only ESCs on 4% PEG-86% PCL-10% cPCL displayed a relevant level of expression. The effect of dorsomorphine, however, was seen to be significantly enhanced on low fiber density 4% PEG-86% PCL-10% cPCL, but not PCL, when compared to control. These results further support low fiber density 4% PEG-86% PCL-10% cPCL as a substrate for enhanced differentiation of ESCs to physiologically-relevant, functional cardiomyocytes.

Example 18

Cross-Linked Hydrogels

A copolymer of 90% PCL-10% cPCL was synthesized following the process described in Example 4. PEG-dihydrazides were synthesized with two different molecular weights ($M_w$) of PEG ($M_w$=2000 or 6000 Da). Confirmation of the existence of the amine-functionalized product was verified with Fourier Transform Infrared (FTIR) spectroscopy. The reactive carboxyl groups on the polymers were cross-linked to primary amine groups of PEG-dihydrazides by 1-ethyl-3-(3-dimethylaminopropyl)carbodiimide) (EDCI) coupling.

The pore architecture was optimized through salt leaching and lyophilization methods used previously (Sung et al. *Eur. Cells Mater.* 2008; 15:77-86). Briefly, polymers were dissolved in N-methylpyrrolidone (NMP) with 10% tetrahydrofuran (THF) and mixed with EDCI and a small amount of methylene chloride for the cross-linking reaction. This solution mixture was poured over a dish of polymer solution containing sodium chloride crystals between 212-425 µm in size and stirred briefly. Then the mixture was left at room temperature for 30 minutes to allow for cross-linking. The salt-filled hydrogel was then frozen in liquid nitrogen and lyophilized to create micropores from the phase separation of the THF blowing agent. Lyophilized scaffolds were then incubated in water for four days to remove salts, leaving a porous structure. Hydrogel scaffolds were dessicated for two days and sputter coated with gold for 120 seconds for scanning electron microscopy (SEM) analysis of porous structure using a Hitachi S-4200 Scanning Electron Microscope at 1 kV accelerating voltage and 40× magnification.

Figure 11:
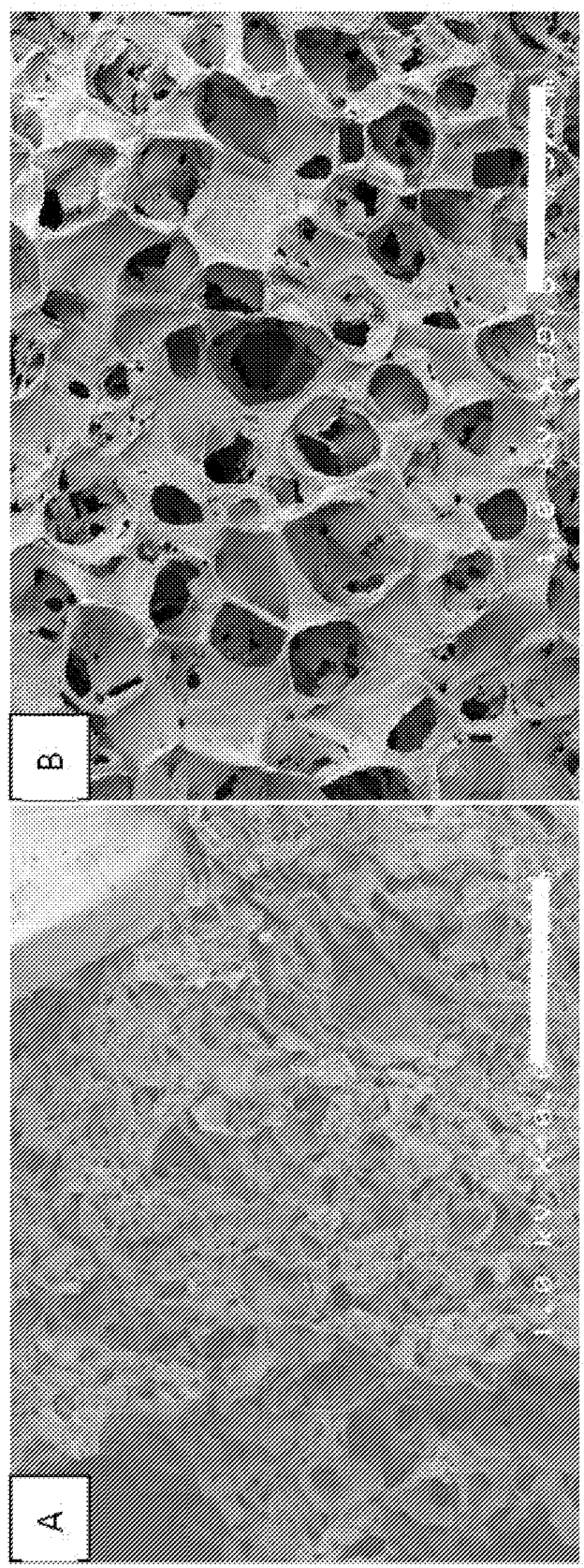
FIG. 11 depicts a series of SEM images of crosslinked hydrogels, produced by both adding 10% THF blowing agent and stiffing the salt/polymer mixture prior to the cross linking reaction. (A) Scaffolds with no crosslinking; (B) Hydrogel cross-linked with PEG (MW=2 kDa) dihydrazides. Scale bar=750 μm.

Macropores and micropores were generated in hydrogels by salt leaching and phase separation of THF blowing agent as shown in FIG. 11. Stirring a polymer solution with salts improved the interconnectivity between macropores noticeably, compared to those resulting from static diffusion of polymer solution into a stack of salts.

Figure 12:
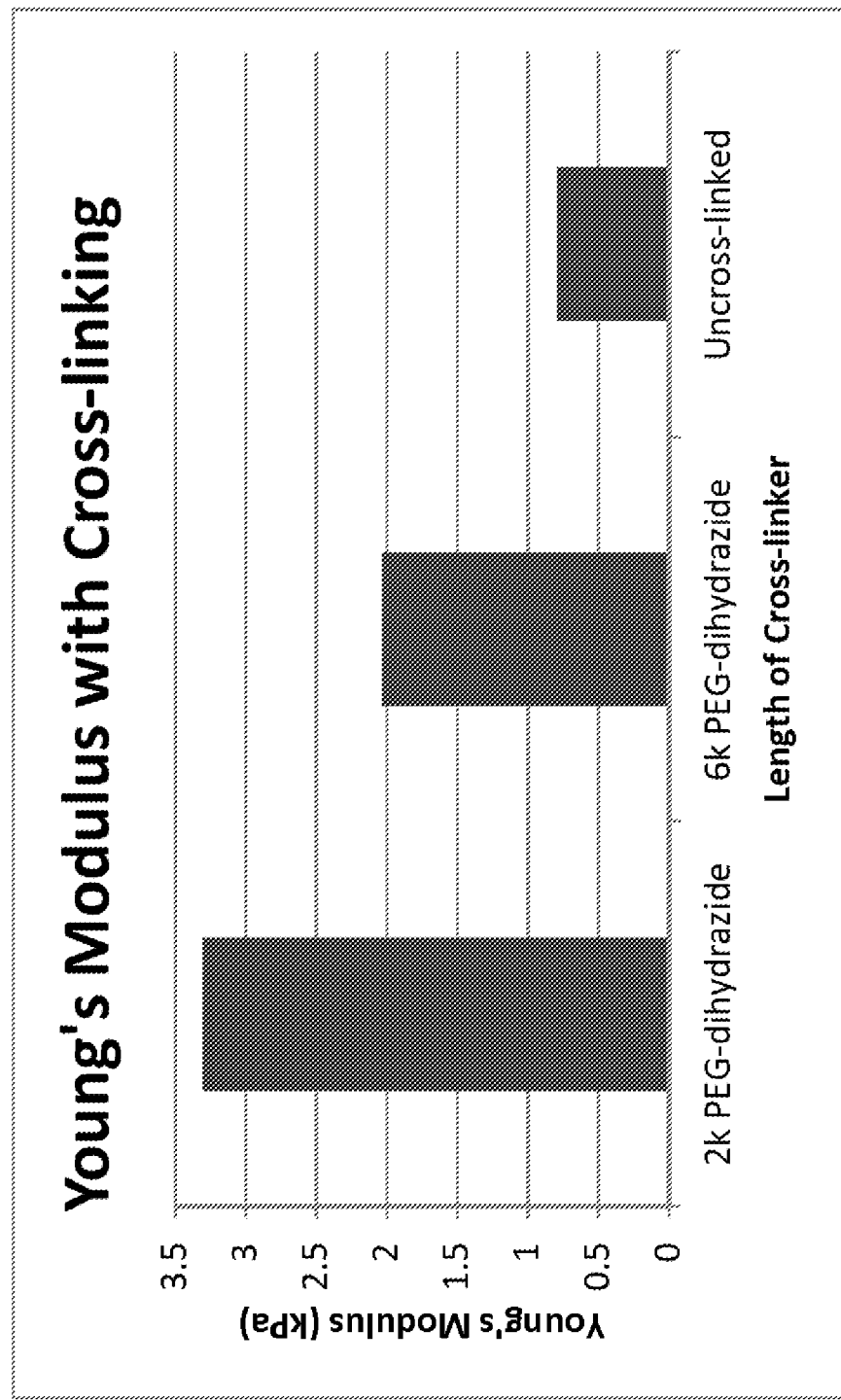
FIG. 12 is a bar graph showing the Young's modulus of hydrogels of 90% PCL-10% cPCL polymers that have been cross-linked with PEG-dihydrazide crosslinkers of varying molecular weights.

Measurement of Young's Modulus: To measure wet modulus, hydrogels were immersed in nanopure water for 24 hours to allow for hydration. A hydrogel sample was clamped to a Bose Instron and the specimen dimension was measured with a digital micrometer. Hydrogels made of the PEG cross-linkers with two different $M_w$ were stretched at a constant stress rate. Load versus displacement was monitored and Young's modulus was calculated from the slope of stress versus strain curve for each scaffold. Scaffolds with no cross-linker were used as a control. The results from mechanical testing showed that the addition of cross-linker molecules increased the modulus more than 1 kPa compared to the uncross-linked control samples (FIG. 12). An increase in the $M_w$ of crosslinkers caused a decrease in the modulus due to increased void volume for water absorption resulting from increased PEG $M_w$.

Example 19

Figure 13:
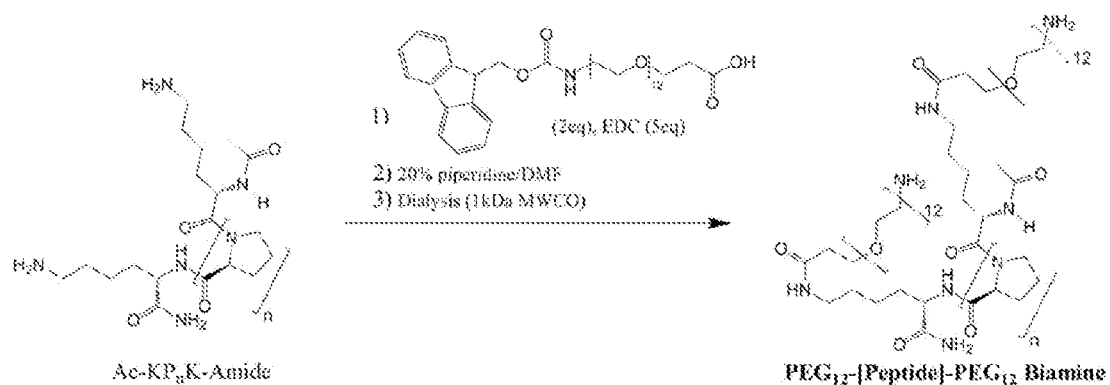
FIG. 13A illustrates the synthesis and characterization of oxidatively-degradable proline oligomers that may be used as crosslinkers. (A) A scheme of the synthesis of lysine-flanked peptides via solid phase peptide synthesis followed by acetylation and cleavage provided an amine at each end of the peptide for coupling of PEG. Deprotection of amines via piperidine produced bisamino-PEG-(Pro)$_n$-PEG crosslinkers. (B) Gel permeation chromatography (GPC) chromatographs of various crosslinkers, each of which show two peaks as detected by UV absorbance (@ 310 nm) for each crosslinker type. The precursor PEG has limited 310 nm absorbance, and therefore, produces no peaks in the region of interest shown.
Figure 13:
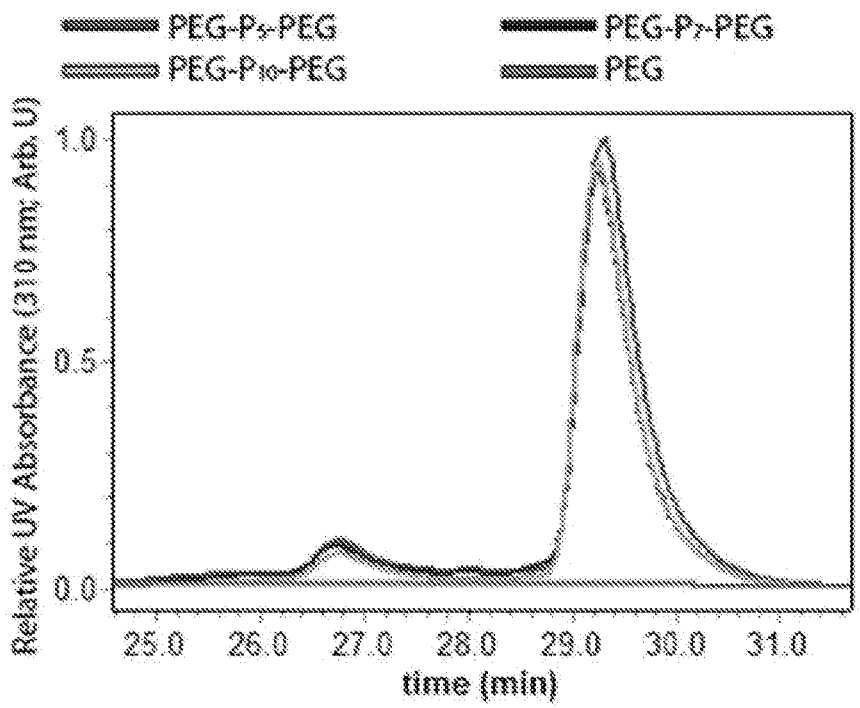

Stimuli-Sensitive Scaffolds for Reactive Oxygen Species-Mediated Controlled Degradation and Release Proline oligomers Ac-KP$_5$K, Ac-KP$_7$K, and Ac-KP$_{10}$K were synthesized by standard Fmoc-chemistry on a Rink amide resin to fashion two free amines for the coupling of Fmoc-PEG$_{12}$-COOH (FIG. 13). 4% PEG-86% PCL-10% cPCL was synthesized as described in Example 5, and contains carboxylic acid groups along the 100 kDa polymer chain for the attachment of the free amines on the cross-linkers. To evaluate the oxidative degradation of the peptides and bi-PEGylated peptides, these materials were incubated for several days at 24° C. or 37° C. with 50 µM $Cu^{2+}$ and 100 mM $H_2O_2$ in PBS. Products were then analyzed by HPLC-MS and GPC. Subsequently, chemically-cross-linked hydrogels of 4% PEG-86% PCL-10% cPCL with equimolar amounts of the PEG-P$_n$-PEG linkers were prepared. The oxidation-dependent material properties of these materials were assessed by mass.

Figure 14:
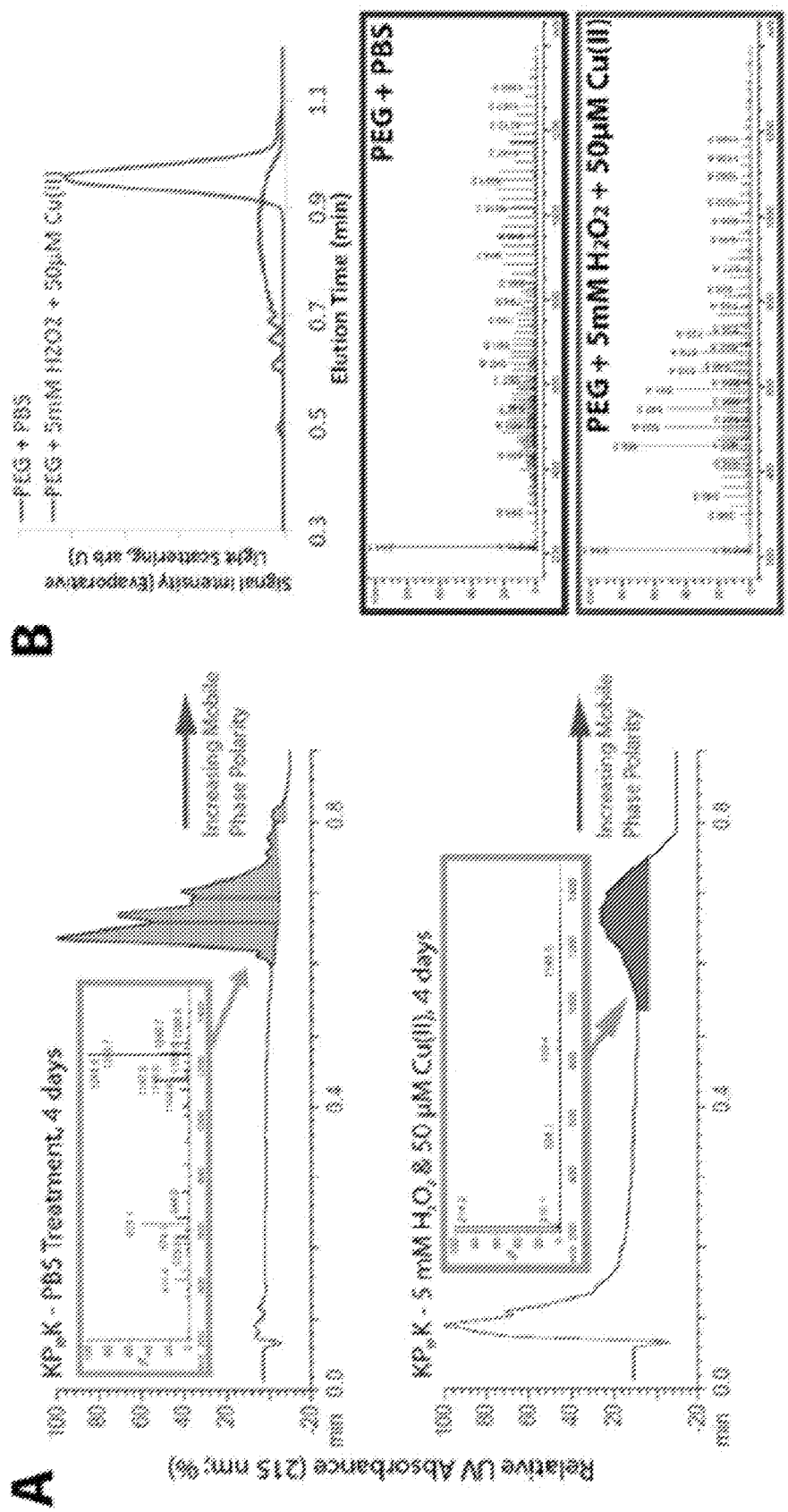
FIG. 14 illustrates results of experiments testing the degradation of proline oligomers in oxidative environments. (A) UV chromatograms (215 nm) and mass spectra of $KP_{10}K$ oligomers after 4 days in either PBS or PBS+5 mM $H_2O_2$+50 μM Cu(II). (B) Evaporative light scattering chromatograms and mass spectra of PEG-dihydrazide treated in either PBS or PBS+5 mM $H_2O_2$+50 μM Cu(II) for 4 days. (C) A graph of the molecular weights of PEG-P$_n$-PEG (n=5, 7 and 10) incubated with PBS+5 mM $H_2O_2$+50 μM Cu(II) as determined by GPC at 0, 2, and 6 days of incubation. $M_n$ values were calculated relative to PEG calibrants.
Figure 14:
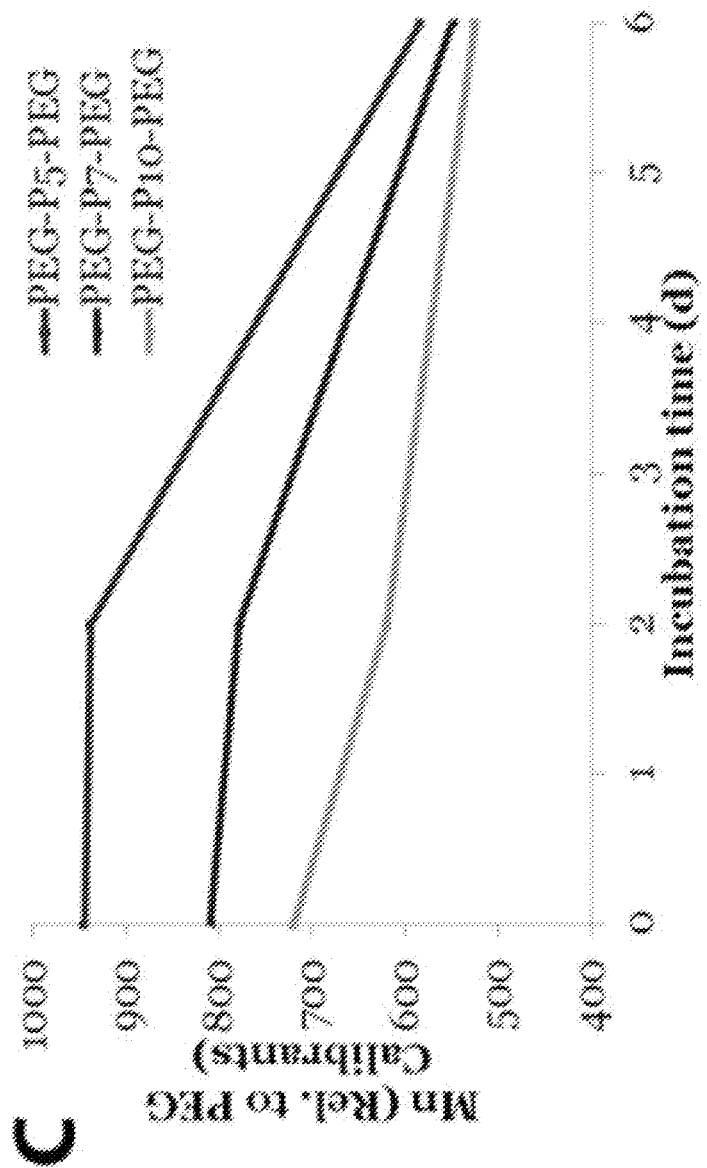

Initially, the degradability of P$_{10}$ oligomers was determined following 4 d in a strongly oxidative environment (5 mM $H_2O_2$+50 µM Cu(II), FIG. 14A). The same treatment was unable to completely degrade PEG-dihydrazide (FIG. 14B), indicating that the use of PEG-P$_n$-PEG crosslinkers would lead to more preferential degradation of the crosslinkers over the peptides. This hypothesis was supported by gel permeation chromatography (FIG. 14C), which demonstrated that the degradation rate of these scaffolds were tuned to some extent by the length of the proline oligomers.

Figure 15:
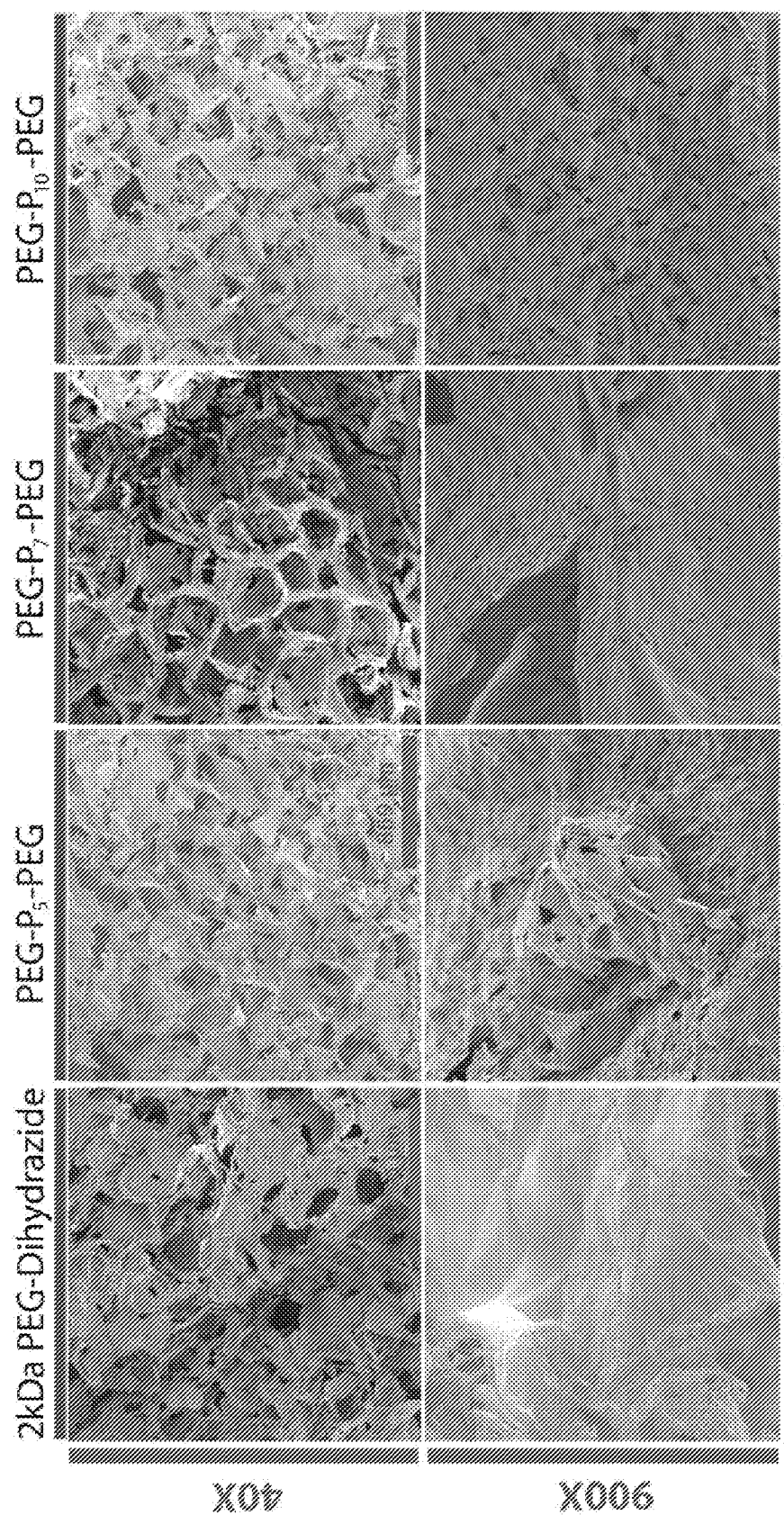
FIG. 15 shows scanning electron micrographs of chemically crosslinked scaffolds of 4% PEG-86% PCL-10% cPCL with either PEG-dihydrazide or various PEG-P$_n$-PEG crosslinkers (n=5, 7 and 10), each at 40× and 900× magnification.

With the oxidative degradability of the crosslinkers confirmed, scaffolds of 4% PEG-86% PCL-10% cPCL were then crosslinked with the PEG-P$_n$-PEG cross-linkers. Scaffolds of macroporous and microporous morphologies were synthesized by mixing pre-polymer (83% terpolymer, 17% PEG-P$_n$-PEG by weight, +carbodiimide, 10% w/v in dichloromethane) over pre-sieved NaCl crystals, curing, drying, and then salt-leaching in nanopure water. Mixing the pre-polymer in dichloromethane—a solvent with limited miscibility with water—alongside carbodiimide activators links the carboxylic groups on the cPCL with the free amines on the cross-linkers. The cross-linking reaction generates water which is immiscible with the dichloromethane, which is then sublimated by freezing and lyophilization of the scaffold. The net result of the two processing conditions (salt leaching and phase separation) results in scaffolds of macroporous and microporous morphology (FIG. 15). The scaffolds crosslinked with PEG-dihydrazide do not exhibit as much microporous morphology due to the surfactant character of PEG, enabling any water in the local environment to be stabilized more effectively from the surrounding dichloromethane medium.

Figure 16:
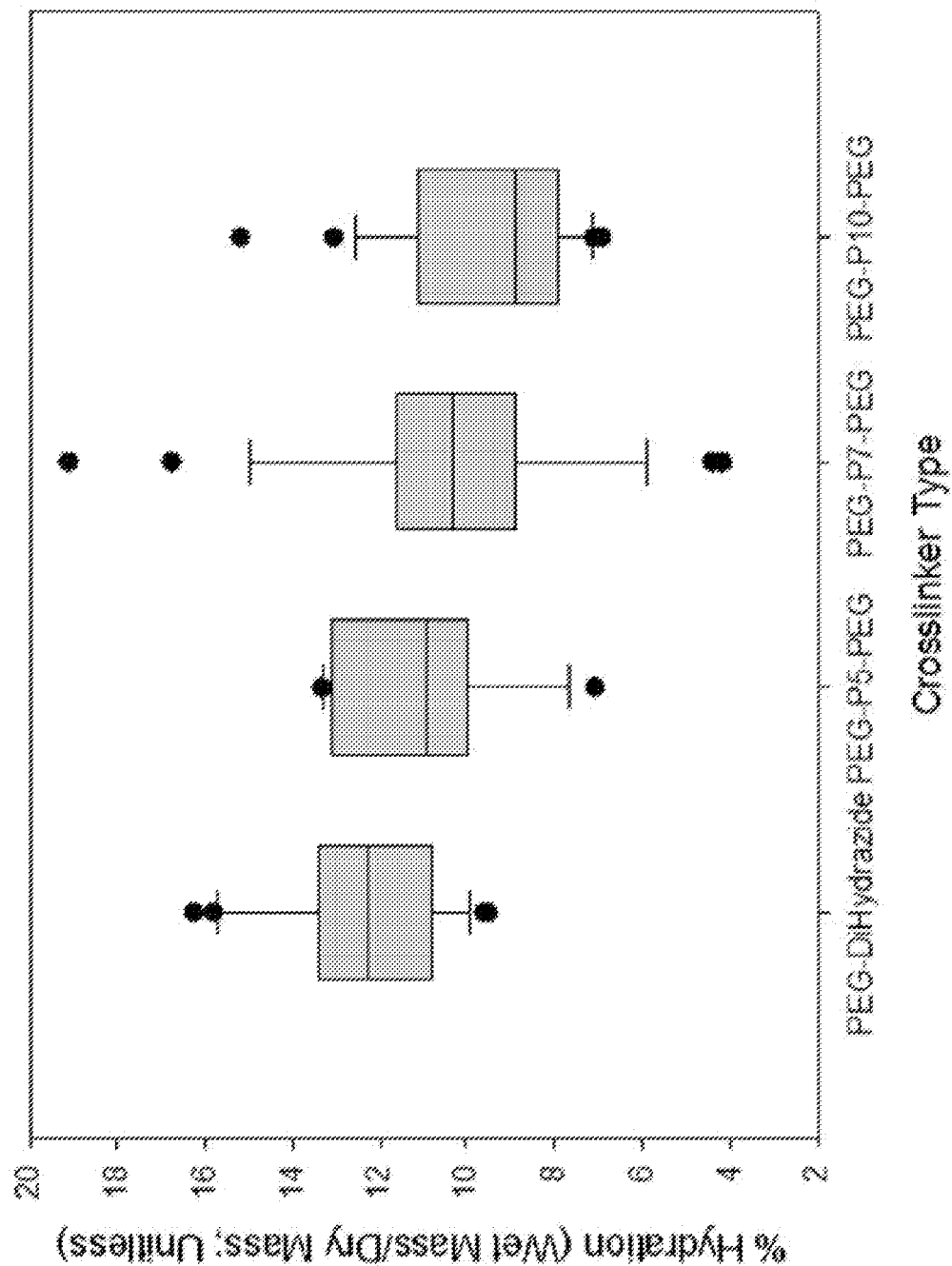
FIG. 16 is a graph of box-and-whisker plots swelling ratios of scaffolds of 4% PEG-86% PCL-10% cPCL that was chemically crosslinked with various PEG-P$_n$-PEG crosslinkers (n=5, 7 and 10). (Each is the average of 24 measurements per crosslinker type). Lines within the boxes indicate the median % hydration value for each scaffold type.

The ability to tune the swelling ratios of the scaffolds in water by varying the lengths of the proline oligomers was also evaluated. As expected, increasing proline content resulted in reduced swelling by the scaffolds by mass, due to the hydrophobic nature of proline (FIG. 16).

Figure 17:
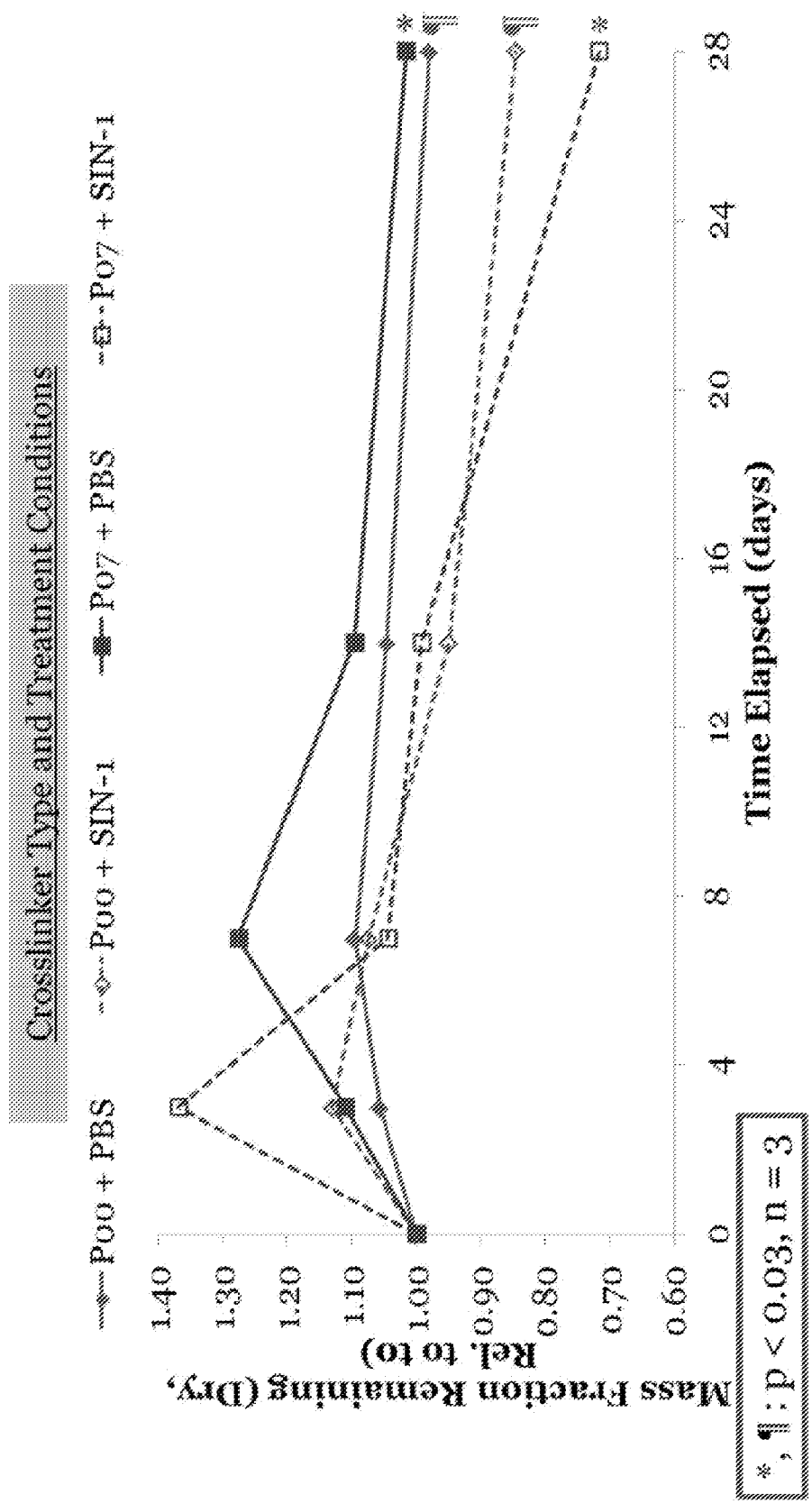
FIG. 17 is a graph showing the mass fraction of scaffolds crosslinked with PEG-dihydrazide (P00) and PEG-P$_7$-PEG (P07), incubated either with PBS or with 1 mM 3-morpholinosydnonimine (SIN-1), over the course of 28 days.

Next, the scaffolds were immersed in a physiological model of oxidative stress or in control salt buffer for 28 days to evaluate their suitability for long-term biomedical applications. To generate an oxidative environment mimicking those in physiological inflammatory scenarios, scaffolds were incubated with 3-morpholinosydnonimine (SIN-1, Invitrogen, Carlsbad, Calif.), which generates superoxide and reactive nitrogen species. To streamline efforts, only PEG-dihydrazide- and PEG-P$_7$-PEG-crosslinked scaffolds were examined. While both scaffolds exhibited some loss of dry mass over the 28-day test period, the scaffolds containing the P$_7$ oligomers demonstrated accelerated mass loss relative to the scaffolds without the peptide (FIG. 17). The loss in mass experienced by scaffolds without the peptide is consistent with earlier data describing the degradation of PEG in oxidative environments (FIG. 14B). Further, the incomplete degradation of the scaffolds is explained by the fact that the scaffolds are synthesized with 83% terpolymer by mass, and PCL has been shown previously to exhibit degradation half-lives of over a year under oxidative conditions.

Proline oligomers and their bisPEGylated counterparts exhibit oxidative degradability. The resulting PEG-P$_n$-PEG crosslinkers have been used to chemically crosslink scaffolds of the base material 4% PEG-86% PCL-10% cPCL, producing scaffolds of widespread macroporous and microporous morphology. These scaffolds are degradable in oxidative environments mimicking physiologic conditions over 28 days, demonstrating their potential applicability to areas of modulation of inflammatory and angiogenic activity, as well as stem cell differentiation.

All patents, publications and references cited herein are hereby fully incorporated by reference. In case of conflict between the present disclosure and incorporated patents, publications and references, the present disclosure should control.

The invention claimed is:
1. A polymer of formula (I):

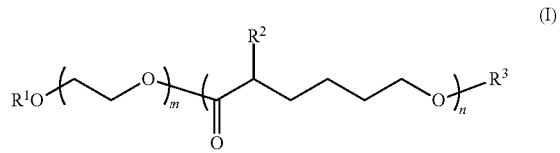

wherein:
R$^1$ is selected from an alkyl, an acyl and an aryl;
each R$^2$ is independently selected from —H and —COOH;
R$^3$ is selected from —H, an alkyl and an aryl;
m is an integer from about 20 to about 200; and
n is an integer from about 200 to about 2000;
wherein at least one of the R$^2$ substituents is —H and at least one of the R$^2$ substituents is —COOH.

2. The polymer of claim 1, wherein R$^1$ is an alkyl.
3. The polymer of claim 2, wherein R$^1$ is methyl.
4. The polymer of claim 1, wherein m is an integer from 40 to 140.
5. The polymer of claim 1, wherein n is an integer from 500 to 1000.
6. The polymer of claim 1, wherein from about 70-95% of R$^2$ substituents are —H and from about 5-30% of R$^2$ substituents are —COOH.
7. The polymer of claim 1, wherein R$^3$ is —H.
8. A composition comprising the polymer of claim 1 and at least one compound covalently attached to the polymer.
9. The composition of claim 8, wherein the at least one compound crosslinks a plurality of polymers.
10. The composition of claim 9, wherein the at least one compound is covalently attached to one or more —COOH moieties.
11. The composition of claim 8, wherein the compound comprises a hydrophilic polymer.
12. The composition of claim 11, wherein the compound comprises poly(ethylene glycol).
13. The composition of claim 12, wherein the compound is poly(ethylene glycol)-dihydrazide.
14. A medical device comprising the polymer of claim 1.
15. The medical device of claim 14, wherein the device is a cardiovascular stent, a cardiac patch, or a catheter.
16. A block copolymer comprising:
at least one hydrophilic polymer block; and
at least one block comprising a random copolymer of ϵ-caprolactone and α-carboxy-ϵ-caprolactone.
17. The block copolymer of claim 16, wherein at least one hydrophilic polymer block comprises poly(ethylene glycol), poly(propylene glycol), poly(vinylpyrrolidone), or a poly (amino acid).
18. The block copolymer of claim 17, wherein the at least one hydrophilic polymer block comprises poly(ethylene glycol).
19. The block copolymer of claim 18, wherein the poly (ethylene glycol) polymer block comprises methoxy-poly (ethylene glycol).
20. The block copolymer of claim 18, wherein the poly (ethylene glycol) polymer block has a molecular weight of about 1000-8000 Da.
21. The block copolymer of claim 16, wherein the random copolymer of ϵ-caprolactone and α-carboxy-ϵ-caprolactone comprises about 70-95% caprolactone moieties and about 5-30% α-carboxy-ϵ-caprolactone moieties.

22. A composition comprising the block copolymer of claim 16 and at least one compound covalently attached to the block copolymer.

23. The composition of claim 22, wherein the at least one compound crosslinks a plurality of polymers.

24. The composition of claim 23, wherein the at least one compound is covalently linked to the α-carboxy groups of α-carboxy-ε-caprolactone.

25. A medical device comprising the block copolymer of claim 16.

26. A method of making a block copolymer comprising:
providing a hydrophilic polymer comprising a terminal hydroxyl group;
reacting said hydrophilic polymer with caprolactone and a catalyst under conditions sufficient to effect ring-opening polymerization of the caprolactone, to form a block copolymer comprising a hydrophilic polymer block and at least one caprolactone block; and
carboxylating the α-carbon of at least one caprolactone moiety.

27. The method of claim 26, wherein the hydrophilic polymer comprises poly(ethylene glycol), poly(propylene glycol), poly(vinylpyrrolidone), or a poly(amino acid).

28. The method of claim 27, wherein the hydrophilic polymer comprises poly(ethylene glycol).

29. The method of claim 28, wherein the poly(ethylene glycol) polymer block comprises methoxy-poly(ethylene glycol).

30. The method of claim 28, wherein the poly(ethylene glycol) polymer block has a molecular weight of about 1000-8000 Da.

31. The method of claim 26, wherein the carboxylating step comprises reacting the block copolymer with a base and carbon dioxide.

* * * * *